United States Patent
Wheeler

(10) Patent No.: US 11,590,326 B2
(45) Date of Patent: Feb. 28, 2023

(54) CHEST TUBE INSERTION SHEATH

(71) Applicant: NAILMARK MEDICAL, LLC, Tallahassee, FL (US)

(72) Inventor: Mark Wheeler, Tallahassee, FL (US)

(73) Assignee: NAILMARK MEDICAL, LLC, Tallahassee, FL (US)

( * ) Notice: Subject to any disclaimer, the term of this patent is extended or adjusted under 35 U.S.C. 154(b) by 789 days.

(21) Appl. No.: 16/290,167

(22) Filed: Mar. 1, 2019

(65) Prior Publication Data

US 2020/0276416 A1     Sep. 3, 2020

(51) Int. Cl.
*A61M 25/06*     (2006.01)
*A61B 17/34*     (2006.01)

(52) U.S. Cl.
CPC ..... *A61M 25/0668* (2013.01); *A61B 17/3421* (2013.01); *A61M 2025/0687* (2013.01)

(58) Field of Classification Search
CPC . A61B 17/3468; A61B 17/34; A61B 17/3415; A61B 17/3421; A61B 17/3439; A61M 27/00; A61M 1/84; A61M 25/0668
See application file for complete search history.

(56) References Cited

U.S. PATENT DOCUMENTS

| | | | |
|---|---|---|---|
| 3,613,684 A | 10/1971 | Sheridan | |
| 4,865,593 A | 9/1989 | Ogawa et al. | |
| 5,059,183 A * | 10/1991 | Semrad | A61M 25/09 604/158 |
| 5,169,387 A * | 12/1992 | Kronner | A61B 17/3415 604/164.06 |
| 5,397,311 A | 3/1995 | Walker et al. | |
| 5,431,676 A * | 7/1995 | Dubrul | A61B 17/3439 606/191 |
| 5,509,909 A * | 4/1996 | Moy | A61B 17/3415 604/170.03 |
| 5,755,693 A | 5/1998 | Walker et al. | |
| 6,224,586 B1 | 5/2001 | Stephens | |

(Continued)

FOREIGN PATENT DOCUMENTS

WO     2008136877 A1     11/2008
WO     2016201570 A1     12/2016

OTHER PUBLICATIONS

PCT/US2020/020562 International Search Report and Written Opinion, dated Jul. 2, 2020, 14 pages.

(Continued)

*Primary Examiner* — Tiffany Legette
(74) *Attorney, Agent, or Firm* — Waller Lansden Dortch & Davis, LLP; Matthew C. Cox

(57) ABSTRACT

A chest tube insertion device includes a semi-rigid curvilinear sheath body having a distal end and a proximal end, a lumen defined axially through the sheath body from the distal end to the proximal end, the lumen including a distal end opening at the distal end and a proximal end opening at the proximal end, and a tapered pneumostatic tube clamp at the distal end of the sheath body, the tube clamp including one or more clamp tabs angled radially inward toward the distal end opening. The chest tube insertion device is supported during insertion into the chest cavity by a stylet. The chest tube insertion device is also removable from a chest tube when a free end of the chest tube is positioned in the chest cavity of a patient.

23 Claims, 23 Drawing Sheets

(56) References Cited

U.S. PATENT DOCUMENTS

| | | |
|---|---|---|
| 6,517,519 B1 | 2/2003 | Rosen et al. |
| 6,837,873 B1 | 1/2005 | Polley et al. |
| 6,966,896 B2 | 11/2005 | Kurth et al. |
| 7,014,626 B2 | 3/2006 | Sanderson |
| 7,708,744 B2 | 5/2010 | Soma et al. |
| 7,758,586 B2 | 7/2010 | Muto et al. |
| 7,819,889 B2 | 10/2010 | Healy et al. |
| 7,824,375 B2 | 11/2010 | Hastings, Jr. et al. |
| 8,137,317 B2 | 3/2012 | Osypka |
| 8,251,975 B2 | 8/2012 | Atkins et al. |
| 9,526,876 B2 | 12/2016 | Kristensen et al. |
| 2002/0042605 A1 | 4/2002 | Castaneda et al. |
| 2003/0163139 A1 | 8/2003 | Graf |
| 2005/0216028 A1* | 9/2005 | Hart .................. A61B 17/3462 606/108 |
| 2006/0041230 A1* | 2/2006 | Davis ................ A61M 25/0009 604/160 |
| 2009/0221965 A1 | 9/2009 | Osypka |
| 2010/0312261 A1 | 12/2010 | Suzuki et al. |
| 2011/0245805 A1* | 10/2011 | Swinehart .......... A61B 17/3421 604/523 |
| 2013/0131549 A1 | 5/2013 | Kristensen et al. |
| 2013/0204087 A1* | 8/2013 | Jaworek ............. A61B 1/00154 600/114 |
| 2014/0207069 A1* | 7/2014 | Bierman ........... A61M 25/0668 604/167.03 |
| 2014/0324000 A1 | 10/2014 | Hill |
| 2018/0199959 A1 | 7/2018 | Lee |

OTHER PUBLICATIONS

EP Search Report for EP Application 20766878.1, Published by European Patent Office dated Nov. 2, 2022.

* cited by examiner

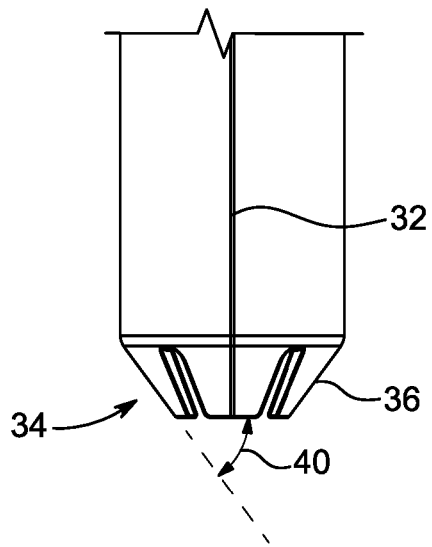 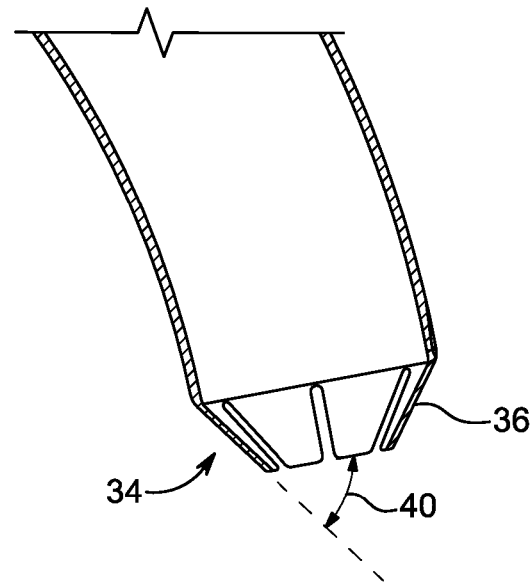
FIG. 8a  FIG. 8b
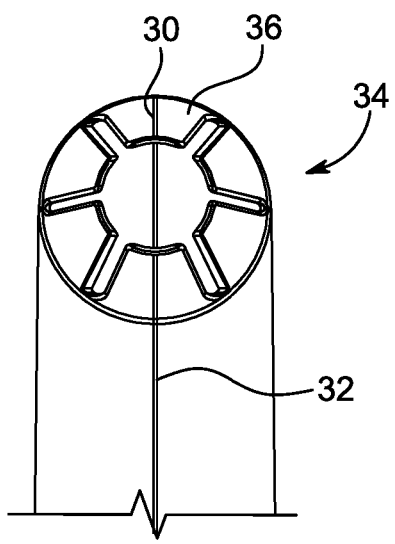 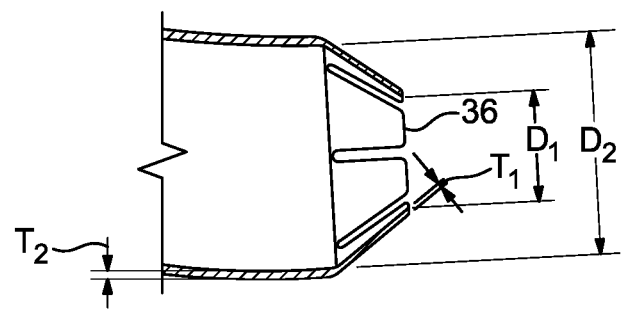
FIG. 8c  FIG. 8d

CHEST TUBE INSERTION SHEATH

A portion of the disclosure of this patent document contains material that is subject to copyright protection. The copyright owner has no objection to the reproduction of the patent document or the patent disclosure, as it appears in the U.S. Patent and Trademark Office patent file or records, but otherwise reserves all copyright rights whatsoever.

CROSS-REFERENCES TO RELATED APPLICATIONS

Not Applicable

STATEMENT REGARDING FEDERALLY SPONSORED RESEARCH OR DEVELOPMENT

Not Applicable

REFERENCE TO SEQUENCE LISTING OR COMPUTER PROGRAM LISTING APPENDIX

Not Applicable

BACKGROUND OF THE INVENTION

The present disclosure relates generally to surgical devices and methods and more particularly to devices and methods of introduction of a chest tube into the chest cavity of a patient.

The use of thoracotomy tubes or chest tubes in clinical medicine dates back to the World War II era. Chest tubes are inserted into the chest cavity to evacuate blood, fluid, air, or infectious material. The chest tube ideally is located in the pleural space defined as the space between the outer lining of the lung (visceral pleura) and the inner lining of the chest wall (parietal pleura). This space is normally a potential space as the area is effectively under vacuum. Air and fluid can be introduced into this space by way of trauma, infection, cancer, and inflammatory conditions among others. Once a tube is appropriately inserted, the tube is attached to a vacuum source and the material is evacuated. This is clinically important to avoid further damage to the lung and allow the lung to re-inflate for proper functioning.

Classically the technique used to insert large bore chest tubes includes the following steps: first, sterile cleaning and draping to the surgical site; second, administering local anesthesia; third, creating an incision at a lateral or superior chest site; fourth, dissecting down through the subcutaneous fat and tissues to reach the rib at the target entry point; fifth, puncturing the intercostal fascia, muscle, and finally the parietal pleura with a large curved hemostat clamp having a blunt tip; sixth, forcibly spreading the clamp jaws to stretch the tissues and create a hole large enough for the tube to pass; seventh, inserting the operator's finger to ensure the opening is proper, the lung is not scarred to the chest wall, and there is adequate space for the tube; eighth, blindly inserting the tube, either with the large clamp initially guiding the tube through the opening, or just advancing the tube itself; and ninth, suturing the tube in place and hooking up to suction.

There are numerous problems with the standard technique and instruments used for insertion of a chest tube into the chest cavity. The intercostal space between the ribs varies greatly from patient to patient, but is often only a small or tight space. There are times that the operator's index finger will hardly fit through the intercostal space as described in the standard technique. Because of the limited space and possible thick adipose tissue under the skin, the guidance of the chest tube can be a challenge.

Generally, the most superior part of the pleural space, or apex, is the desired location for the tip of the tube if there is a pneumothorax. If blood or fluid is to be evacuated, then the base of the pleural space is the best target. Many studies have documented a high complication rate with chest tube placement. The complications vary from malposition of the tube in a fissure to perforation of the heart. The operator has very little control of the tube once it passes between the ribs of the patient. Attempts at turning the tube are often ineffective, and the operator, as a result of the standard procedure, is unaware in which direction the tube is directed. If a chest tube is found to be malfunctioning after insertion, or is malpositioned on a post-procedure chest x-ray, a new tube must be placed via a new insertion site. Current standard of care does not allow for repositioning of an existing chest tube secondary to high risk of infection.

What is needed then are improvements in chest tube insertion devices and methods for surgical procedures.

BRIEF SUMMARY

This Brief Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

One aspect of the disclosure is a chest tube insertion device having a sheath body with proximal and distal ends. The chest tube insertion device also includes proximal and distal openings positioned at the proximal end and the distal end, respectively. A lumen is defined axially through the sheath body from the distal end to the proximal end. A tapered pneumostatic tube clamp is disposed at the distal end of the sheath body, the tube clamp including one or more clamp tabs angled radially inward toward the distal end opening.

Another aspect of the disclosure includes a chest tube insertion device having a first groove on the sheath body extending from the distal end to the proximal end of the sheath body and a second groove on the sheath body extending from the distal end to the proximal end of the sheath body.

A further aspect of the disclosure includes a chest tube insertion device having a first handle and a second handle positioned on the proximal end of the sheath body, the first handle positioned between the first groove and the second groove on a first side of the sheath body and the second handle positioned opposite the first handle between the first groove and the second groove on a second side of the sheath body.

Another aspect of the present disclosure includes a chest tube insertion device disposed about a curvilinear axis.

A further aspect of the present disclosure includes a stylet insertable into a chest tube insertion device. The stylet may include an axial lumen via which a stylet or introducer unit may be inserted or advanced over a wire.

Numerous other objects, advantages and features of the present disclosure will be readily apparent to those of skill in the art upon a review of the following drawings and description of a preferred embodiment.

BRIEF DESCRIPTION OF THE DRAWINGS

FIGS. 8a-8d are various views of an embodiment of a pneumostatic tube clamp positioned on a chest tube insertion device.

DETAILED DESCRIPTION

Figure 1:
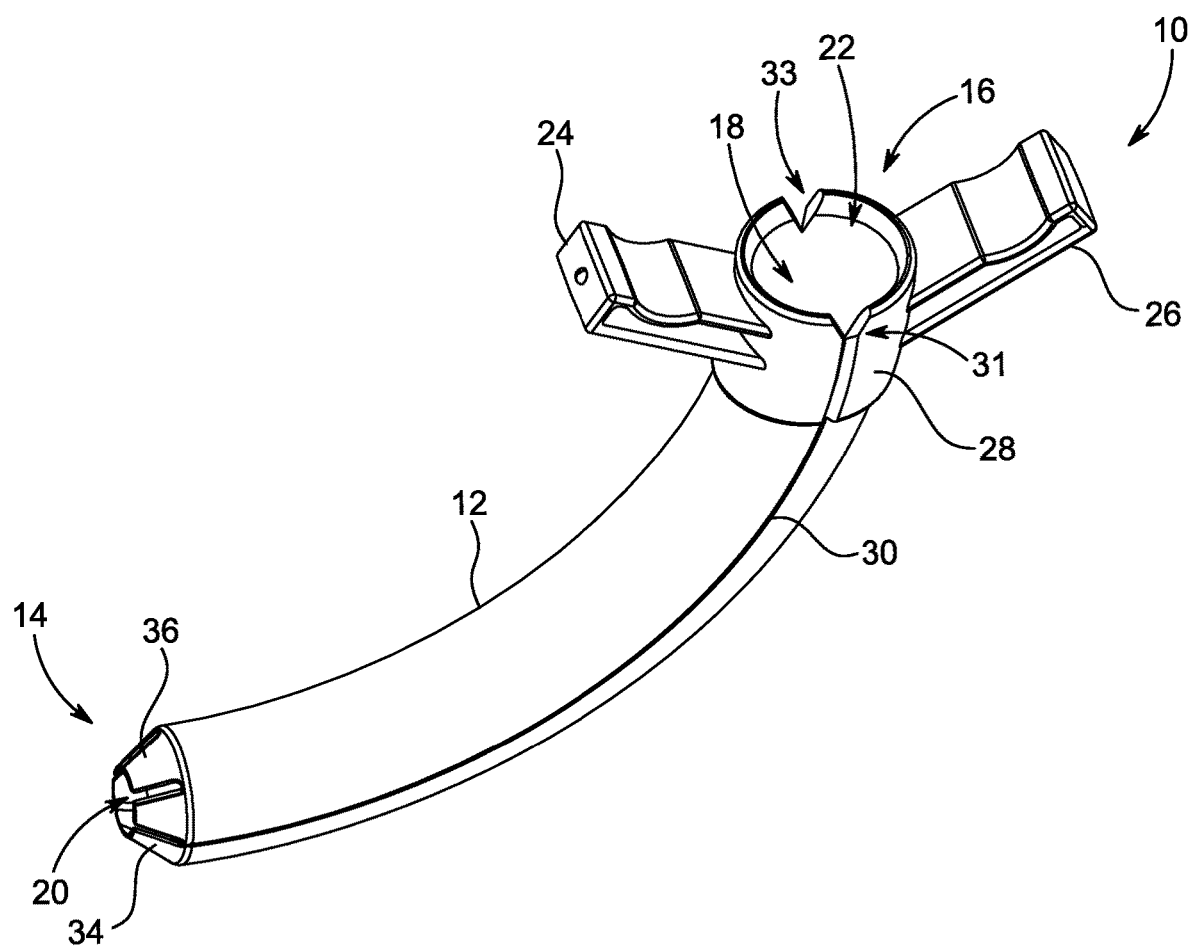
FIG. 1 is a perspective view of an embodiment of a chest tube insertion device.

While the making and using of various embodiments of the present invention are discussed in detail below, it should be appreciated that the present invention provides many applicable inventive concepts that are embodied in a wide variety of specific contexts. The specific embodiments discussed herein are merely illustrative of specific ways to make and use the invention and do not delimit the scope of the invention. Those of ordinary skill in the art will recognize numerous equivalents to the specific apparatus and methods described herein. Such equivalents are considered to be within the scope of this invention and are covered by the claims.

In the drawings, not all reference numbers are included in each drawing, for the sake of clarity. In addition, positional terms such as "upper," "lower," "side," "top," "bottom," etc. refer to the apparatus when in the orientation shown in the drawing. A person of skill in the art will recognize that the apparatus can assume different orientations when in use.

The present disclosure provides a chest insertion sheath apparatus for use in surgical procedures including but not limited to chest tube insertions. As shown in FIG. 1, an embodiment of a chest tube insertion device 10 includes sheath body 12 having a distal end 14 and a proximal end 16. The distal end 14 of the sheath body 12 is the end that is insertable into chest cavity of the patient. The proximal end 16 of the sheath body 12 is handled or manipulated by the user.

Referring again to FIG. 1, the chest tube insertion device 10 further includes a lumen 18 or bore defined axially through the insertion device 10 from the distal end 14 to the proximal end 16. The lumen 18 includes a distal end opening 20 at the distal end 14 of the insertion device 10 and a proximal end opening 22 at the proximal end 16 of the insertion device 10. The lumen 18 is defined in the insertion device 10 such that the lumen 18 and the insertion device 10 are defined about a first axis 15. When the chest tube insertion device 10 has been surgically installed into the patient's chest cavity, the user may insert a chest tube 150 through the lumen 18 such that the chest tube 150 is introduced into the patient's chest cavity.

With further reference to FIG. 1, the insertion device 10 may further include a tube clamp 34 positioned at the distal end 14 of the sheath body 12. The tube clamp 34 may be tapered. The tube clamp 34 is operable to provide resistance to axial movement of a chest tube 150 relative to the chest tube insertion device 10 when the chest tube 150 is inserted into the proximal opening 22, through the lumen 18, and out the distal opening 20. The tube clamp 34 is positioned such that the tube clamp 34 contacts the chest tube 150 when disposed through the distal opening 20. In one embodiment, the tube clamp 34 includes one or more clamp tabs 36 angled radially inward toward the distal opening 20. Thus, when the chest tube 150 is installed in the insertion device 10 and in contact with the tube clamp 34, a threshold force must be applied to the chest tube 150 in order for the chest tube 150 to move relative to the insertion device 10. The radial orientation of the flexible tabs 36 allows for the engagement of multiple chest tube sizes and diameters. Additionally, the tube clamp 34 provides relative pneumostasis when suction is applied to the chest tube 150 while it remains engaged with the chest tube insertion device 10. This allows for a chest x-ray to be obtained with the chest tube 150 on suction, thus giving a real time assessment of the tube's 150 position and function before the chest tube insertion device 10 is removed. If the tube's 150 position is not satisfactory, the suction can be stopped, then the tube 150 can be partially withdrawn until the distal tip of the tube 150 is within the chest tube insertion device 10. Then, the chest tube insertion device 10 can be turned and repositioned followed by readvancement of the chest tube 150. The chest tube insertion device 10 acts as a barrier between the tube 150 and skin of the patient during repositioning.

Again referring to FIG. 1, the insertion device 10 may further include a first groove 30 and a second groove 32. The first groove 30 may be on the insertion device 10 extending from the distal end 13 to the proximal end 16 of the insertion device 10. The second groove 32 may likewise be on the insertion device 10 extending from the distal end 14 to the proximal end 16 of the insertion device 10. The first groove 30 and the second groove 32 may be a fracture, or parting, line. The first groove 30 and the second groove 32 may be milled into the sheath body 12 or they may be designed into the product such as would be obvious to one of skill in the art, including molds having the grooves in injection molding and in the design for production in additive manufacturing settings. Regardless of the manufacturing, the first groove 30 and the second groove 32 may be positioned opposite each other relative to the lumen 18. The first groove 30 and the second groove 32 provide a portion of the insertion device 10 which is positioned to allow tears to form between a sheath body first portion 12a and a sheath body second portion 12b, such that the tears extend from the proximal end 16 to the distal end 14, when desired. In one embodiment, a user may remove the distal end 14 of the sheath body 12 from the patient's chest cavity while maintaining the chest tube 150 in the chest cavity. The sheath body 12 may be removed from the chest tube 150, which is still disposed in the lumen 18 of the insertion device 10, by tearing the insertion device 10 via the first groove 30 and the second groove 32.

In some embodiments, the grooves 30, 32 may include a V-shape. The V-shaped grooves 30, 32 may be disposed at an angle of 30 degrees to 80 degrees. In some embodiments, the angle of the V-shaped grooves 30, 32 may be at an angle of 45 degrees to 70 degrees. In other embodiments, the angle of the V-shaped grooved may be at an angle of 60 degrees. The angle of the V-shaped grooves 30, 32 may be operable to promote separation of the first and second portions of the sheath body 12a, 12b, while maintaining the integrity of the sheath body 12 while the separation would be undesirable.

Referring further to FIG. 1, the sheath body 12 may further include a first handle 24 and a second handle 26. The first handle 24 and the second handle 26 may be positioned on the proximal end of the sheath body 12. The first handle 24 and the second handle 26 may be positioned opposite each other relative to the lumen 18. In some embodiments, the first handle 24 is positioned on the sheath body first portion 12a between the first groove 30 and the second groove 32. The second handle 26 may be positioned on the sheath body second portion 12b between the first groove 30 and the second groove 32 opposite the first handle 24 relative to the lumen 18. A user may use the first handle 24 and the second handle 26 to manipulate the sheath body 12 into the patient's chest cavity and when it is surgically installed in the chest cavity. Likewise, a user may use the first handle 24 and the second handle 26 to grasp and tear the sheath body 12 via the first groove 30 and the second groove 32.

In some embodiments, the handles 24, 26 may be positioned on a collar 28 of the sheath body 12. The collar 28 may be a portion of the sheath body 12 at the proximal end 16. When the sheath body 12 is injection molded, the collar 28 may be formed such that the sidewalls of the sheath body 12 are thicker at the proximal end 16, the thicker portions of the sidewalls forming the collar 28. In some embodiments, the first and second grooves 30, 32 extend from the distal end 14 to the proximal end 16, including the collar 28. In order to allow the separation of the first portion 12a and the second portion 12b of the sheath body 12 via the first and second grooves 30, 32, some embodiments may include a first notch 31 and a second notch 33. The first notch 31 is positioned on the first groove 30 at the proximal end 16 of the insertion device 10 and the second notch 33 is positioned on the second groove 32 at the proximal end 16 of the sheath body 12. The notches 31, 33 are configured to provide a starting point for tearing the sheath body 12 into two portions 12a, 12b.

In some embodiments, the notches 31, 33 may include a V-shape. The V-shaped notches 31, 33 may be disposed at an angle of 30 degrees to 80 degrees. In some embodiments, the angle of the V-shaped notches 31, 33 may be at an angle of 45 degrees to 70 degrees. In other embodiments, the angle of the V-shaped notches 31, 33 may be at an angle of 50 degrees. The angle of the V-shaped notches 31, 33 may be operable to promote separation of the first and second portions of the sheath body 12a, 12b, while maintaining the integrity of the sheath body 12 while the separation would be undesirable.

Figure 2:
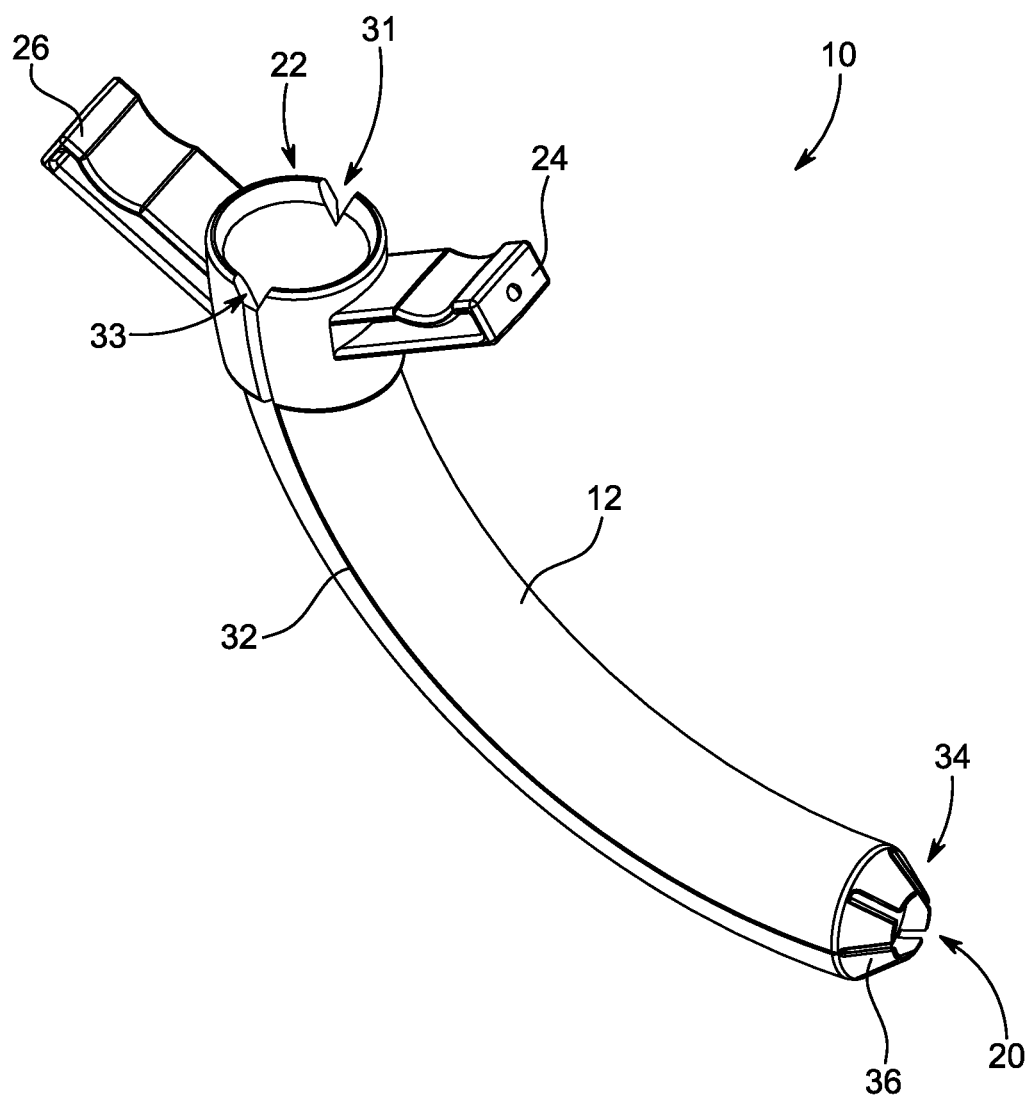
FIG. 2 is an alternate perspective view of an embodiment of a chest tube insertion device.

FIG. 2 provides an alternate view of the embodiment demonstrated in FIG. 1. As can be seen, the second groove 32 may be positioned similarly on the sheath body 12 as the first groove 30, but in a position opposite the first groove 32 relative to the lumen 18.

Figure 3:
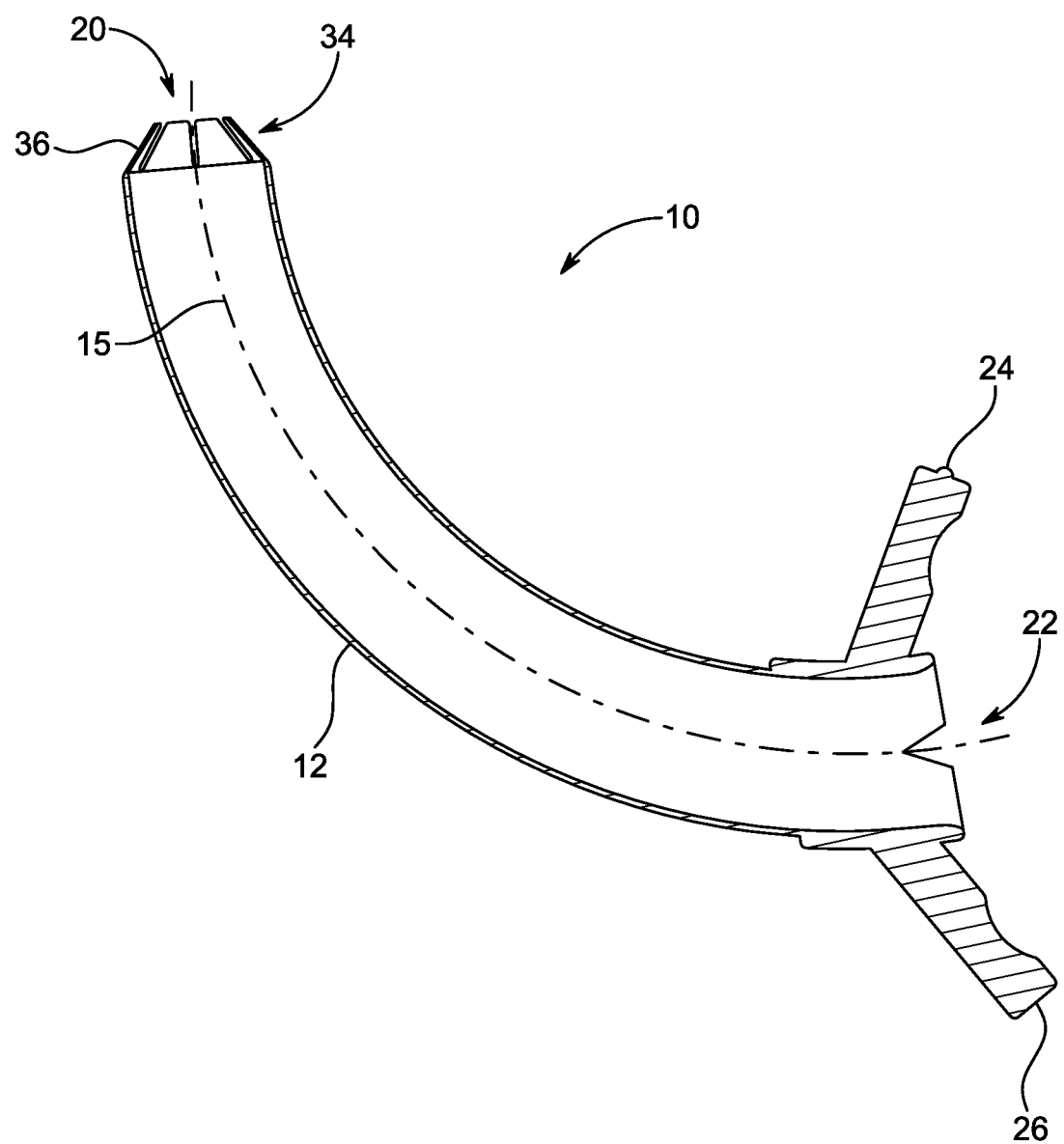
FIG. 3 is a sectional side view of an embodiment of a chest tube insertion device.

Now referring to FIG. 3, the sheath body 12 and the lumen 18 are disposed about a first axis 15. In some embodiments the first axis 15 is curvilinear. When the insertion device 10 is formed of a rigid or semi-rigid material, the curvilinear shape of the insertion device 10 allows a user to position the distal end 14 of the sheath body 12 inside the target cavity, such as a chest cavity, with increased accuracy and precision. A user may manipulate the insertion device 10 via the handles 24, 26 on the proximal end 16 to insert and rotate the curvilinear and rigid insertion device 10 into the chest cavity of a patient in order to position the chest tube 150 in the desired position for optimum functioning. The insertion device 10 may have a curvilinear shape that allows for the turning of the chest tube 150 under the rib 200 then hugging the underside of the chest wall for desired positioning and avoidance of lung fissures or deflection off the lung.

Figure 4:
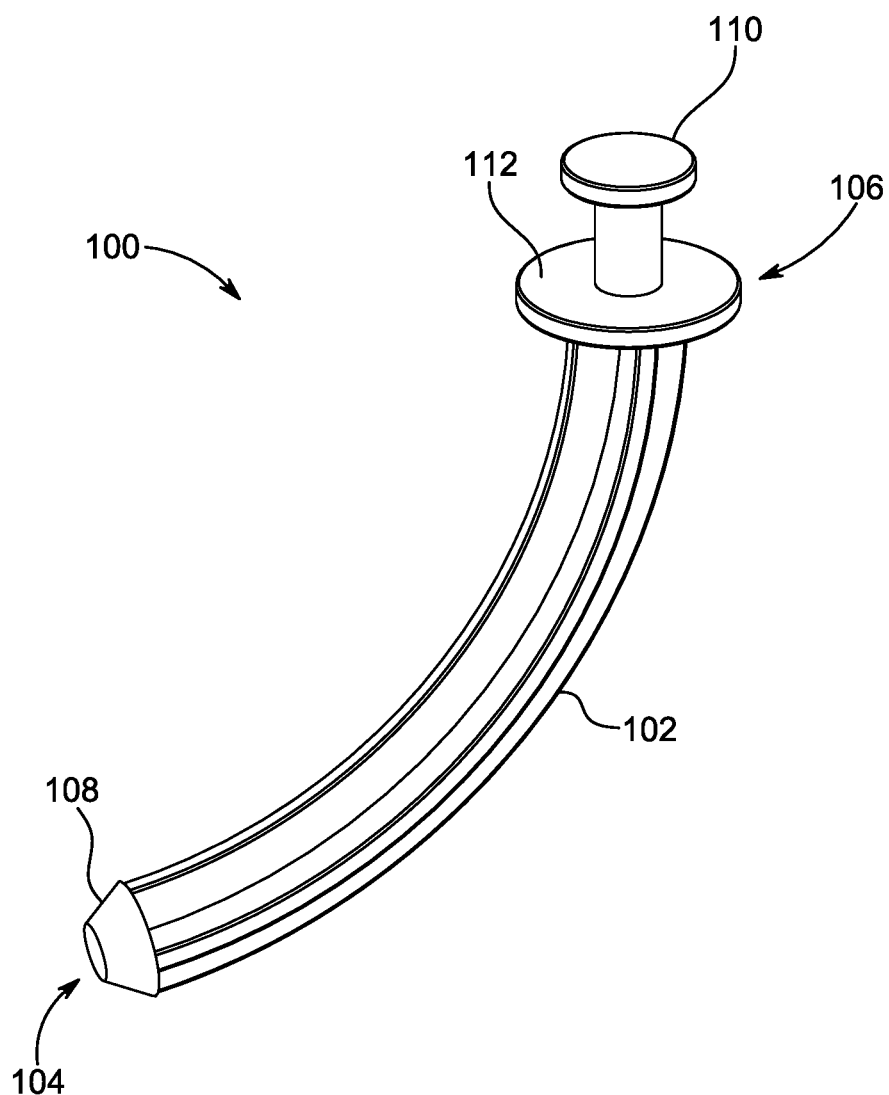
FIG. 4 is a perspective view of an embodiment of a stylet.

Referring now to FIG. 4, a stylet 100 is provided having a stylet body 102, a distal end 104, and a proximal end 106. The stylet 100 may further comprise a grip 110 disposed on the proximal end 106 and a flange 112 positioned on the stylet 100 between the grip 110 and the stylet body 102. The stylet 100 is insertable into the insertion device 10. Specifically, the stylet 100 may be inserted into the lumen 18 of the sheath body 12. The stylet 100 is operable to provide support to the insertion device 10 during the process of inserting the insertion device 10 into the chest cavity of a patient. In some instances, even when the insertion device 10 is formed of a rigid material, the insertion of the device 10 into the chest cavity may be met with resistance due to narrow intercostal space between the ribs or due to difficult tissue to navigate such as thick layers of adipose tissue. The stylet 100 is operable to reinforce the insertion device 10 during insertion into the desired space and during manipulation of the insertion device 10 into the desired position such that the distal end 14 of the insertion device 10 is positioned proximate the location for tube suction.

Referring further to FIG. 4, the stylet body may be formed to include ridges extending radially outward from the center of the stylet body 102. In other embodiments, the stylet 100 may be formed into a variety of shapes, which would allow the stylet 100 to support the sheath body 12 during insertion and manipulation. In the embodiment shown in FIG. 4, the stylet 100 includes a diameter substantially equal to or slightly less than the diameter of the lumen 18, thus allowing the stylet 100 to be positioned in the lumen 18 of the insertion device 10.

Figure 5:
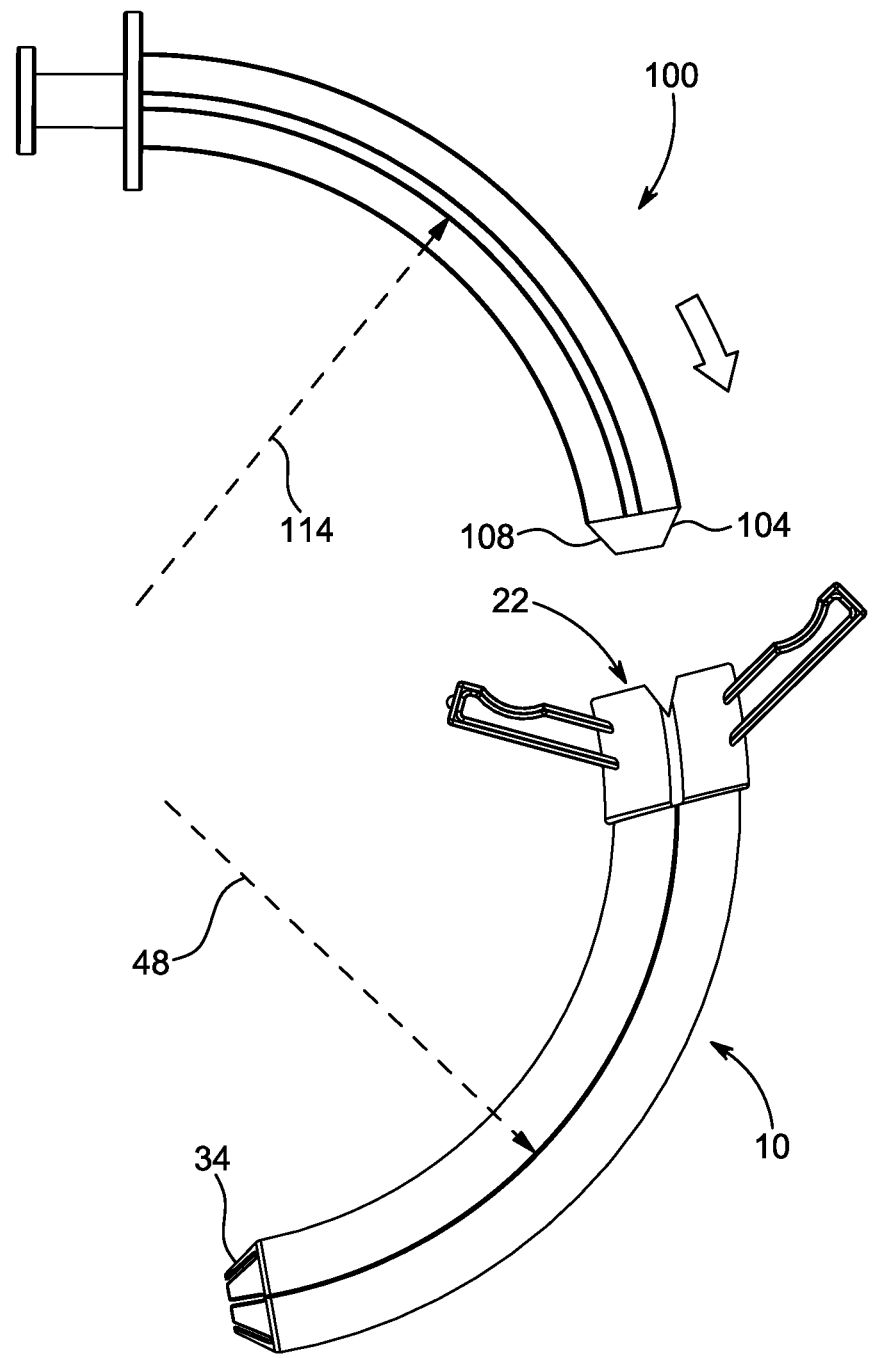
FIG. 5 is a side view of an embodiment of a stylet being inserted into a chest tube insertion device.

Now referring to FIG. 5, the stylet 100 may installed into the insertion device 10 by feeding the distal end 104 of the stylet 100 into the lumen 18 at the proximal opening 22 of the insertion device 10. The stylet 100 may be translated along the axis 15 of the insertion device 10 until the flange 112 contacts the proximal end 16 of the insertion device 10. In some embodiments, the insertion device 10 and the stylet 100 may be curvilinear. The stylet 100 may be arced such that the stylet 100 is curved, the arc being formed at a distance offset from a center point, the distance comprising a stylet radius 114. Likewise, the insertion device 10 may be arced such that the insertion device 10 is curved, the arc being formed at a distance offset from a center point, the distance comprising a sheath radius 48. In some embodiments, the stylet radius 114 and the sheath radius 48 are approximately the same.

Figure 6:
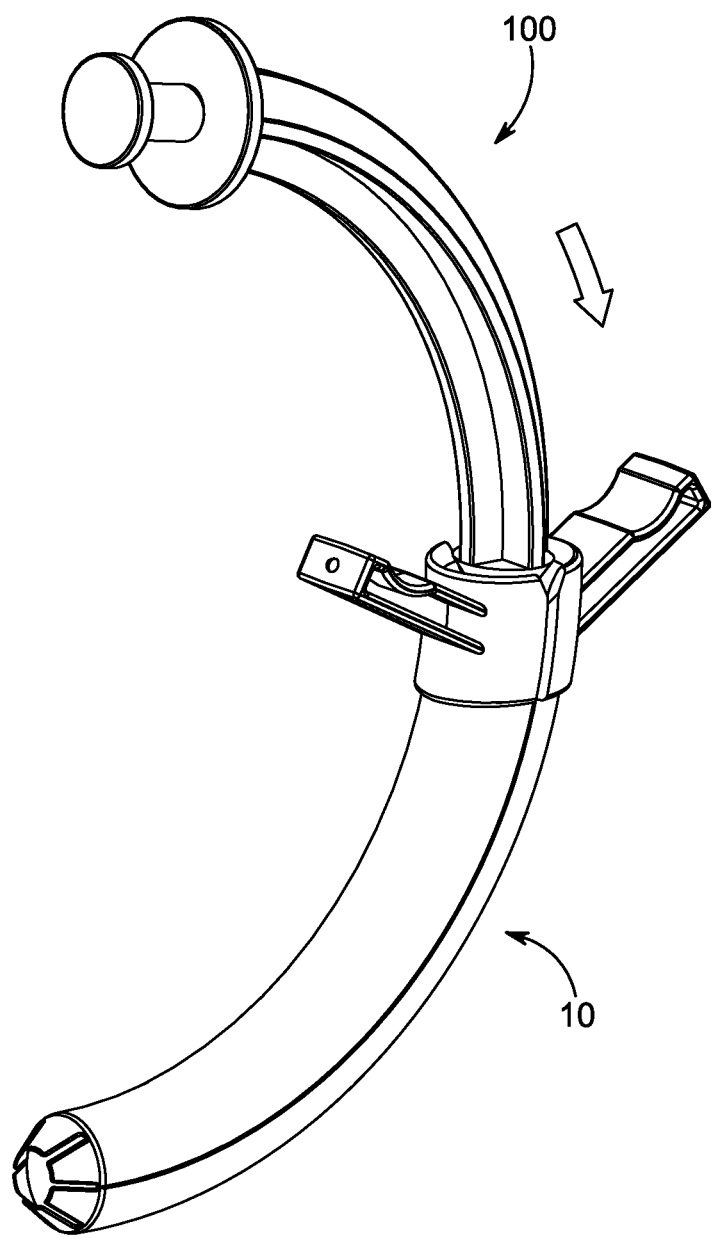
FIG. 6 is a perspective view of an embodiment of a stylet being inserted into a chest tube insertion device.
Figure 7:
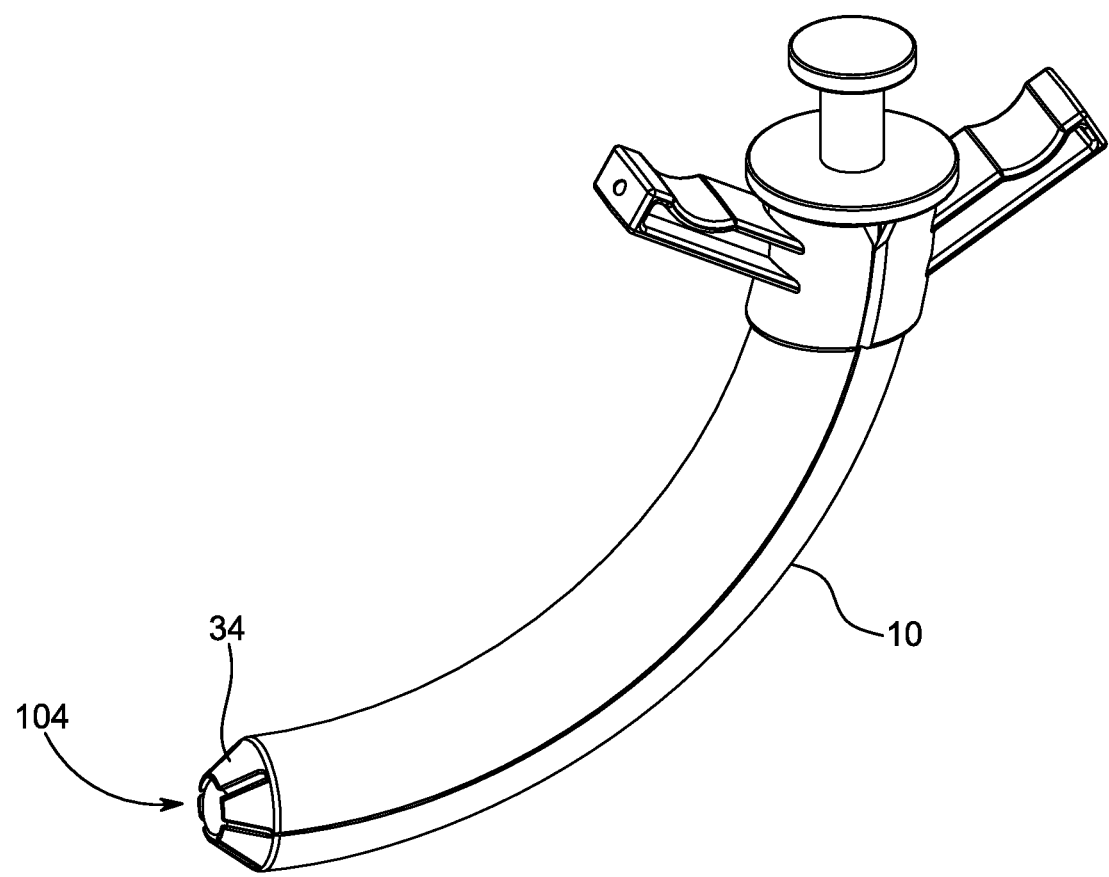
FIG. 7 is a perspective side view of an embodiment of a stylet and chest tube insertion device, where the stylet is fully installed in the insertion device.

Referring now to FIGS. 5-7, the stylet 100 may also include a clamp support 108. When the stylet 10 is fully installed in the insertion device 10, the clamp support 108 contacts the tube clamp 34. The flange 112 of the stylet 100 prevents the clamp support 108 from extending out through the distal opening 20 of the insertion device 10. When the insertion device 10 is being inserted into the patient, the clamp support 108 prevents the tube clamp 34 from being deflected inward. This allows the distal end 14 to move through the patient's tissue without accumulating any of the tissue or fluids in the lumen 18 of the insertion device 10 and it minimizes the snagging and damage to the tissue that can be caused by using the insertion device 10 to probe and explore for the appropriate position for insertion and placement of the chest tube 150. The clamp support 108 may be positioned on the distal end 104 of the stylet 100 such that the angle between the stylet body 102 and the clamp support 108 match the clamp tab angle 40 of the insertion device 10.

With reference to FIGS. 8a-8d, the insertion device 10 in some embodiments may include a tube clamp 34 positioned at the distal end 13 of the sheath body 12. The tube clamp 34 is operable to provide resistance to axial translation of a chest tube 150 relative to the insertion device 10 when the chest tube 150 is positioned in the lumen 12 and extends through the distal opening 20. The resistance provided by the tube clamp 34 may be overcome with a threshold force. This allows the chest tube 150 to be positioned in the insertion device 10 without the chest tube 150 freely extending or retracting through the insertion device 10. The tube clamp 34 may include a second function. More specifically, the tube clamp 34 may provide relative pneumostasis when the tube 150 is on suction while the insertion device 10 is still engaged.

Still referring to FIGS. 8a-8d, the tube clamp 34 may include one or more clamp tabs 36. Each clamp tab 36 may extend from the sheath body and may be angled radially inward toward the distal end opening 20. The clamp tabs 36 may be angled relative to the sheath body 12 at the distal end 14 toward the center of the distal end opening 20 such that the angle formed between the sheath body 12 and the clamp tabs 36 is greater than 0 degrees and less than 180 degrees. The angle formed is the tab angle 40. In some embodiments, the tab angle 40 is greater than 90 degrees and less than 180 degrees. In other embodiments, the tab angle 40 is approximately 135 degrees. The tab angle 40 may be adjusted to a variety of angles in order to provide various utility features, including varying levels of resistance and clamping force on the chest tube 150. However, the clamp tabs 36 may be positioned on the insertion device 10 such that when a chest tube 150 extends through the distal opening 20, the clamp tabs 36 contact the chest tube 150 and the chest tube 150 remains uncollapsed. This may be further facilitated by the clamp tabs 36 being semi-flexible. The tube clamp 34 is positioned distally so pneumostatsis may be maintained even as the insertion device 10 is withdrawn and removed. In other embodiments, the tube clamp 34 may be positioned along the insertion device 10 at various points axially spaced from the distal tip of the insertion device 10.

Referring specifically to FIGS. 8b and 8d, in some embodiment the clamp tabs 36 may be dimensioned such that the clamp tab wall thickness T1 is less than the sheath body wall thickness T2. For example, in some embodiments where the insertion device 10 is extruded or injection molded, the wall thickness of the insertion device 10 decreases at the clamp tabs 36 relative to the sheath body 12. This may allow for greater flexion at the tube clamp 34, thus allowing the tube clamp 34 to engage a chest tube 150 without collapsing the chest tube 150.

Referring again to FIGS. 8a-8d, in some embodiments the clamp tabs 36 may be separated from each other by a clamp tab gap 38. The clamp tab gaps 38 allow the clamp tabs 36 to be deflected radially outward from the resting position. The material rigidity of the clamp tabs 36 will determine the force with which the clamp tabs 36 retain the chest tube 150 in the insertion device 10. Likewise, the clamp tabs 36 may include clamp tab hinges 42. The clamp tab hinges 42 may be disposed proximate the sheath body 12. When the insertion device 10 is a single, injection-molded device, the clamp tab hinges 42 may be a living hinge. Thus, the tube clamp 34 may accommodate chest tubes of various sizes and may provide various levels of resistance as a function of the clamp tabs 36, the clamp tab gaps 38, the clamp tab angle 40, and the clamp tab hinges 42, alone or in various combinations.

Furthermore, the clamp tab gaps 38 allow for the clamp tabs 36 to flex in order to provide a variable diameter of the distal end 14 of the insertion device 10. Because the tabs 36 are angled relative to the body 12, the distal opening 20 is defined by a first diameter D1 that is less than the diameter of the body D2, when the clamp tabs 36 are in a resting or neutral position. Because the clamp tabs 36 are capable of flexion and/or pivoting about the tab hinge 42, the diameter D1 at the distal opening 20 is variable. Thus, the clamp tabs 36 in a neutral position will define a neutral position or first diameter D1 of the distal opening 20 and a variable diameter, which is different from the first diameter, during flexion. See FIG. 16b for example of flexion of clamp tabs 36. The clamp tab gaps 38 likewise prevent the stretching, tearing, and deformation of the distal end 14 of the insertion device 10 when a chest tube 150 having an outer diameter greater than the first diameter (when the tabs 36 are in a neutral or resting position) of the distal opening 20 when the chest tube 150 is advanced through the distal opening 20 of the insertion device 10.

Again referring to FIGS. 8a-8d, the tube clamp 34 may act as a pneumostatic valve, as previously discussed. In some embodiments, the tube clamp 34 may prevent fluid communication between two volumes including the pleural space 204. Air leaks during insertion, positioning, and retraction of the insertion device 10 and chest tube 150 may result in negative or undesirable states and clinical outcomes. Thus, the tube clamp 34 may likewise be referred to as a pneumostatic tube clamp 34 in some embodiments.

In some embodiments, the first and second grooves 30, 32 extend through the clamp tabs 36. This permits a user to remove the insertion device 10 from the chest tube 150 when the chest tube is appropriately positioned in the patient's chest cavity. With the grooves 30, 32 extending the full length of the insertion device 10, including the clamp tabs 36, the user is able to conveniently remove the insertion device 10 without disturbing and displacing the chest tube 150

Figure 9:
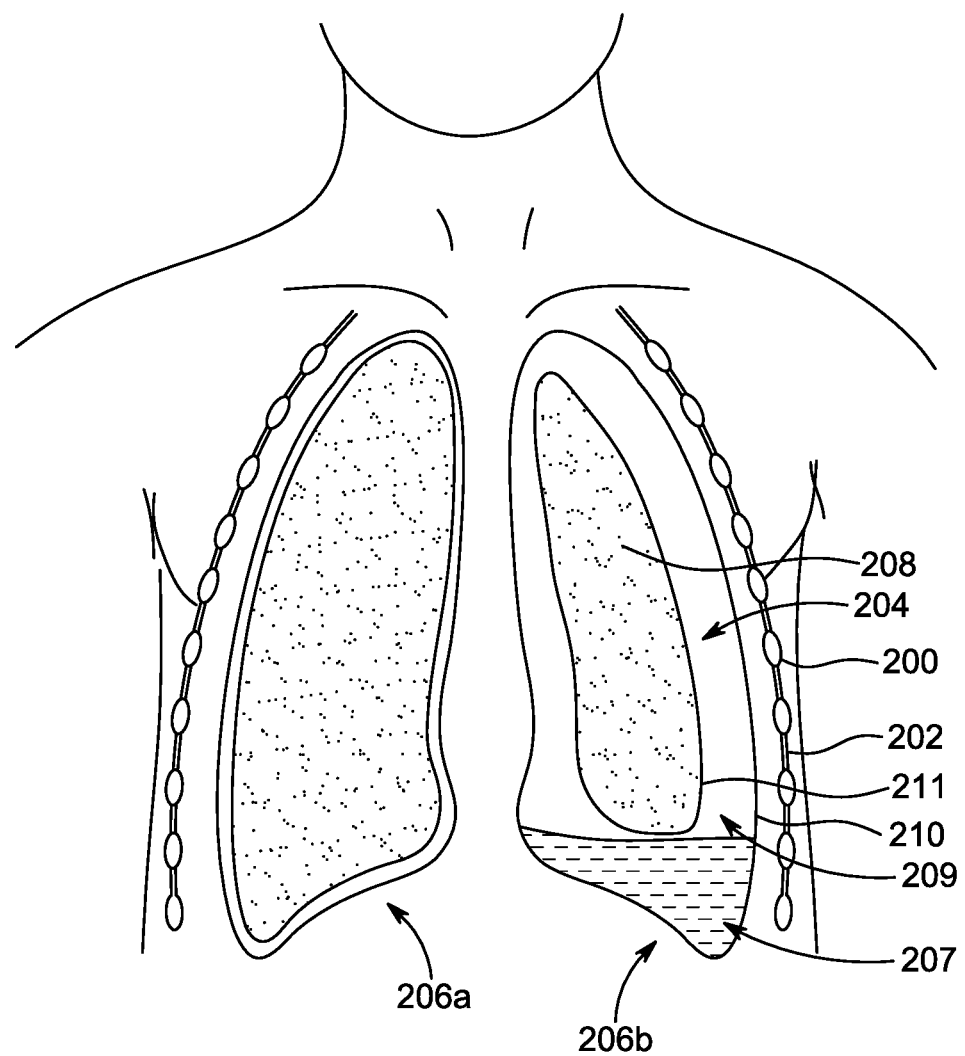
FIG. 9 is a cut-away view of a patient's chest and lungs, where the patient's right lung includes a normal, inflated lung and pleural space and the patient's left lung is a collapsed lung with adverse pleural space pathology.

Now referring to FIGS. 9-20, the chest cavity of a patient is provided. The chest cavity includes a rib 200, an intercostal space 202, a pleural cavity 204, a lung 206, and a normal lung fissure 208. FIG. 9 demonstrates generally the relative positions of the recited anatomy. More specifically, FIG. 9 demonstrates a patient with a first normally inflated lung 206a and a second deflated or collapsed lung 206b. The collapsed lung 206b may be due to the introduction or formation of fluid 207 or air 209 into the pleural cavity 204. The fluid 207 or air 209 or both may become trapped in the pleural cavity 204, which is bounded medially by the visceral pleura 200 and laterally by the parietal pleura 210. This clinically results in a pneumothorax if air 209 is trapped in the pleural cavity 204 or a pleural effusion if fluid 207 is trapped. On occasion, both fluid 207 and air 209 may be present. At least one method of removing the fluid 207 or air 209, and thus treating, are disclosed herein.

Figure 10:
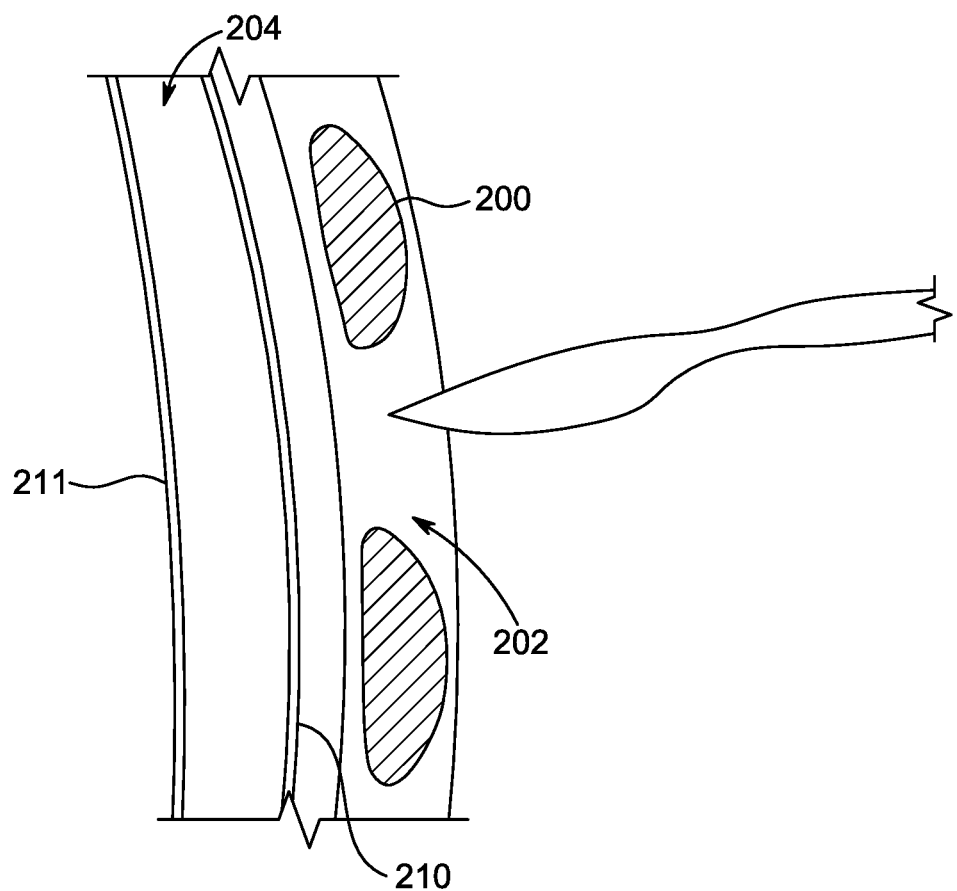
FIG. 10 is a sectional view of an incision being formed in the intercostal space of a patient.
Figure 11:
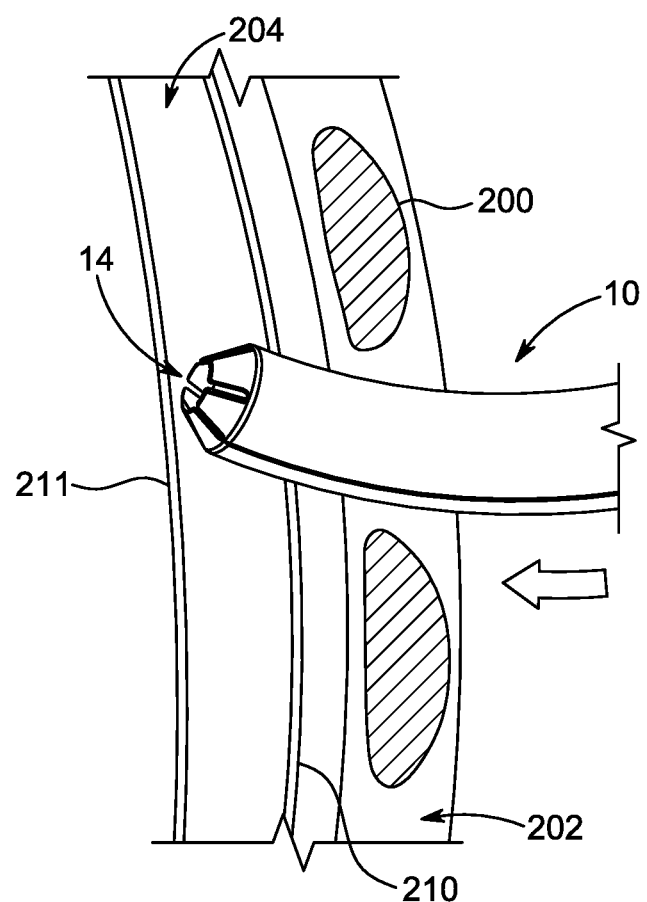
FIG. 11 is a perspective view of an embodiment of a chest tube insertion device being inserted into the pleural space through the intercostal space, wherein a stylet is installed in the insertion device during the insertion process.

Referring now to FIG. 10, a user may begin the insertion of the chest tube 150 by creating an incision through the skin and intercostal space 202 between the ribs 200. FIG. 11 demonstrates the insertion of the distal end 14 of the insertion device 10 through the intercostal space 202 and into the pleural cavity 204. The insertion device is advanced through the intercostal space 202 until the distal end 14 of the insertion device 10 is correctly positioned in the pleural cavity 204. In some embodiments, the insertion device 10 is advanced until the collar 28 is contacting the skin of the patient, such that the insertion device 10 is unable to advance further through the intercostal space 202.

Figure 12:
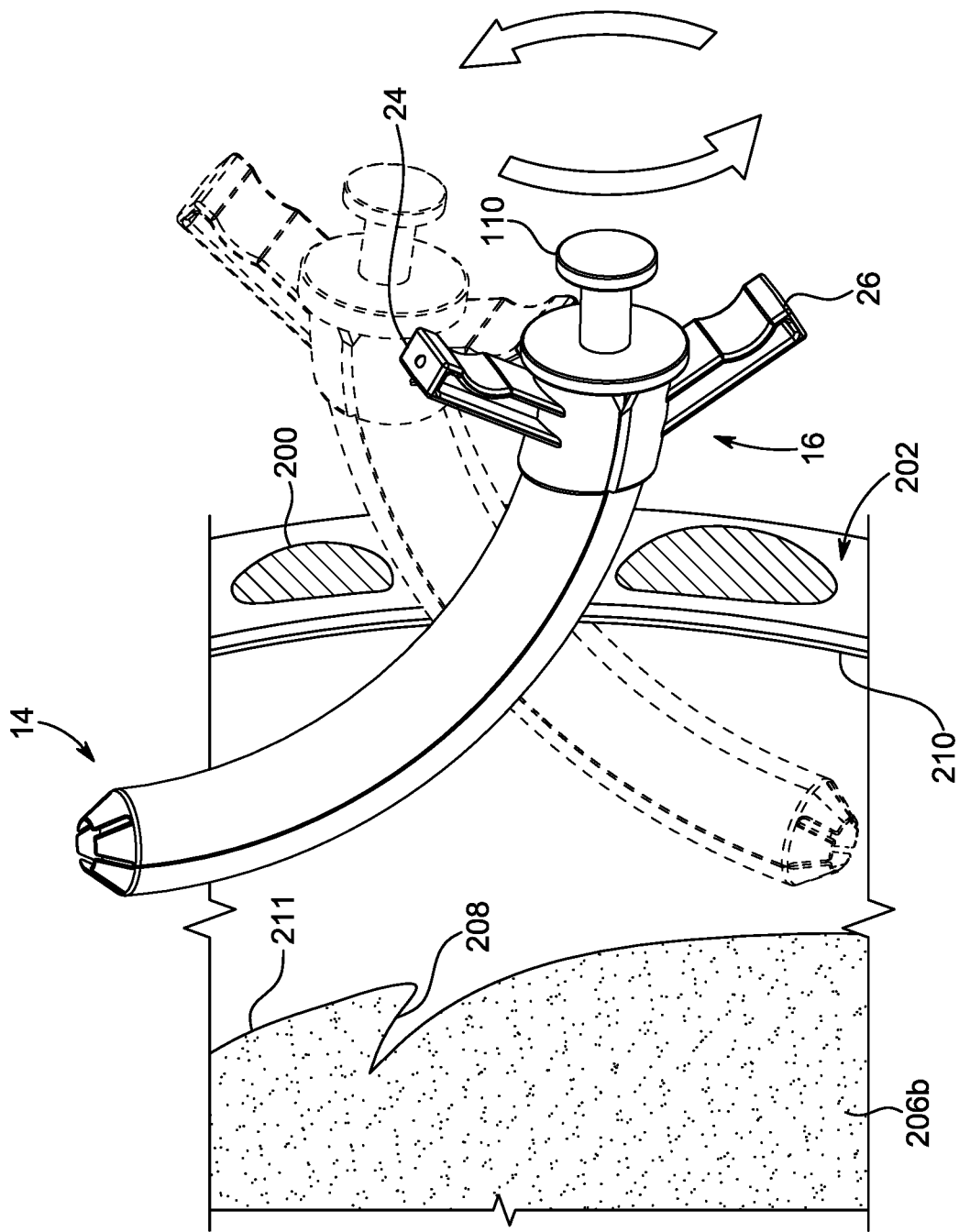
FIG. 12 is a perspective view of an embodiment of a chest tube insertion device being articulated within the pleural space of a patient.
Figure 13:
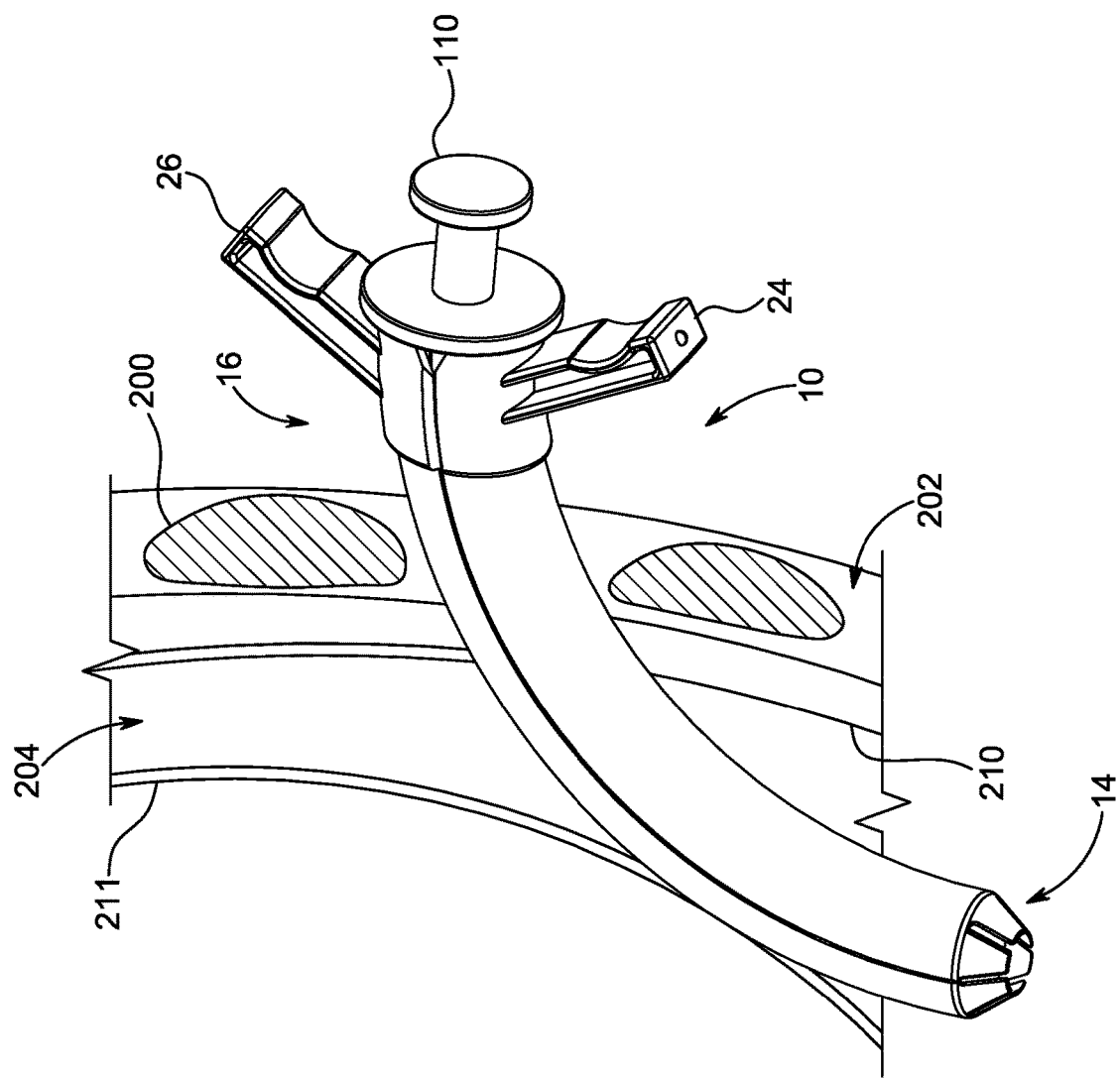
FIG. 13 is a perspective view of an embodiment of a chest tube insertion device after being articulated to a second position in the pleural space of a patient.

Now referring to FIGS. 12 and 13, once the insertion device 10 is inserted between the intercostal space 202, the proximal end 14 of the insertion device 10 may be positioned in the pleural space 204 by adjusting the insertion device 10 via the handles 24, 26. For example, in some embodiments the sheath body 12 may be rotated in order to orient the distal opening 20 of the insertion device 10 in the superior or inferior, anterior or posterior, medial or lateral directions, or a combination thereof. A user may manipulate or orient the insertion device 10 by rotating the insertion device 10 via the handles 24, 26. In those embodiments in which the insertion device 10 is oriented about a curvilinear axis, the proximal end 16 may be rotated allowing the distal end 14 to be repositioned or translated within the pleural space 204. This allows the distal end 14 of the insertion device 10 to be repositioned without having to articulate or pivot the proximal end 16 of the insertion device 10 within the intercostal space 202, thus preventing additional damage to the tissues located in or near the intercostal space 202 and the pleural space 204.

Figure 14:
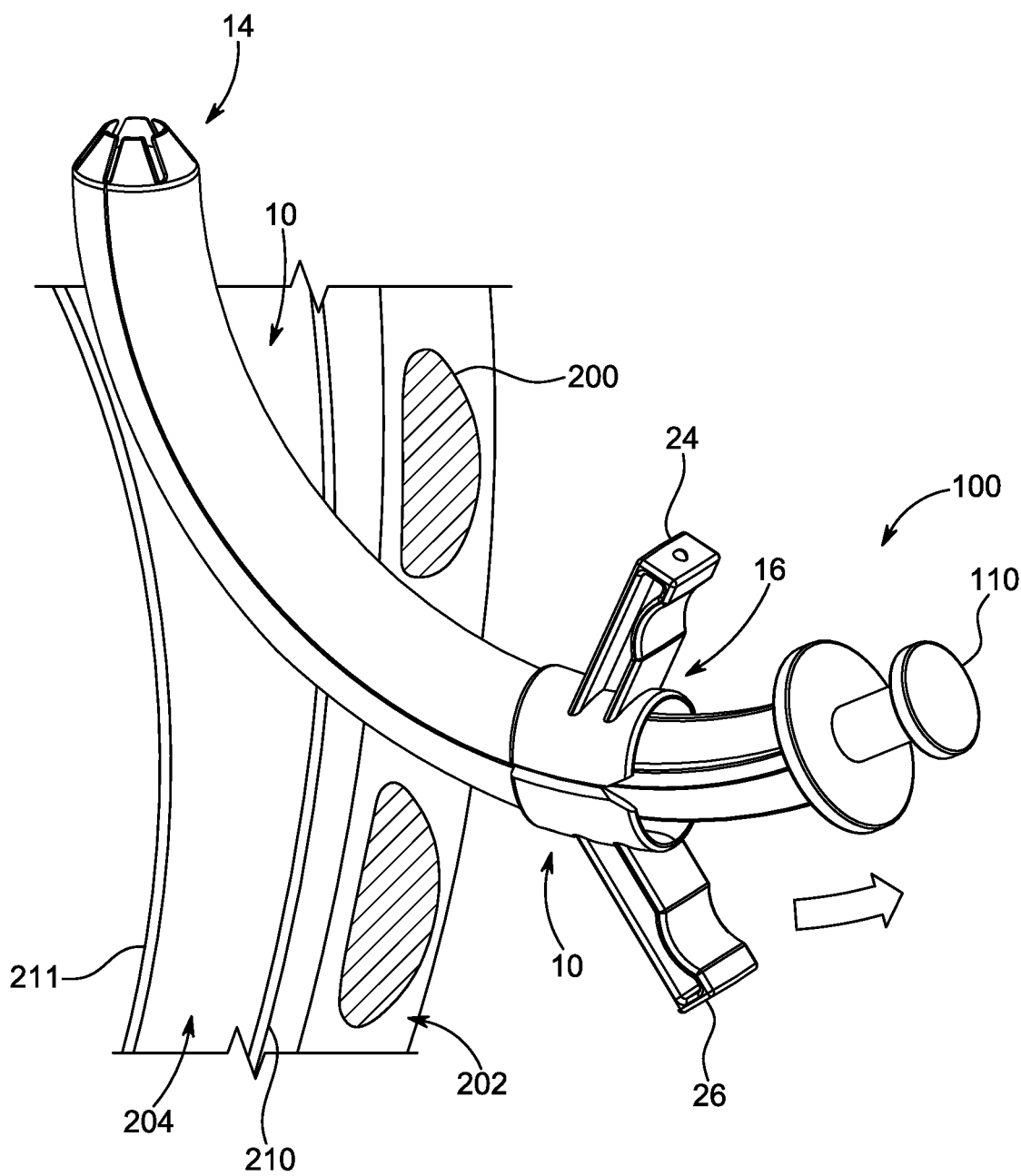
FIG. 14 is a perspective view of an embodiment of a chest tube insertion device in which the stylet is being removed from the insertion device.

Referring to FIG. 14, once the distal end 14 of the insertion device 10 is properly positioned, the user may remove the stylet 100 from the lumen 18 of the insertion device 10. The stylet 100 may be removed by grasping the grip 110 of the stylet 100 and translating the stylet 100 along the axis 15 relative to the insertion device 10, thus the insertion device 10 remains in the desired position while the stylet 100 is removed. In those embodiments in which the stylet 100 and the insertion device 10 are disposed about a curvilinear axis 15, the stylet 10 is operable to slide relative to the insertion device 10, thus evacuating the lumen 18 of the insertion device 10.

Figure 15:
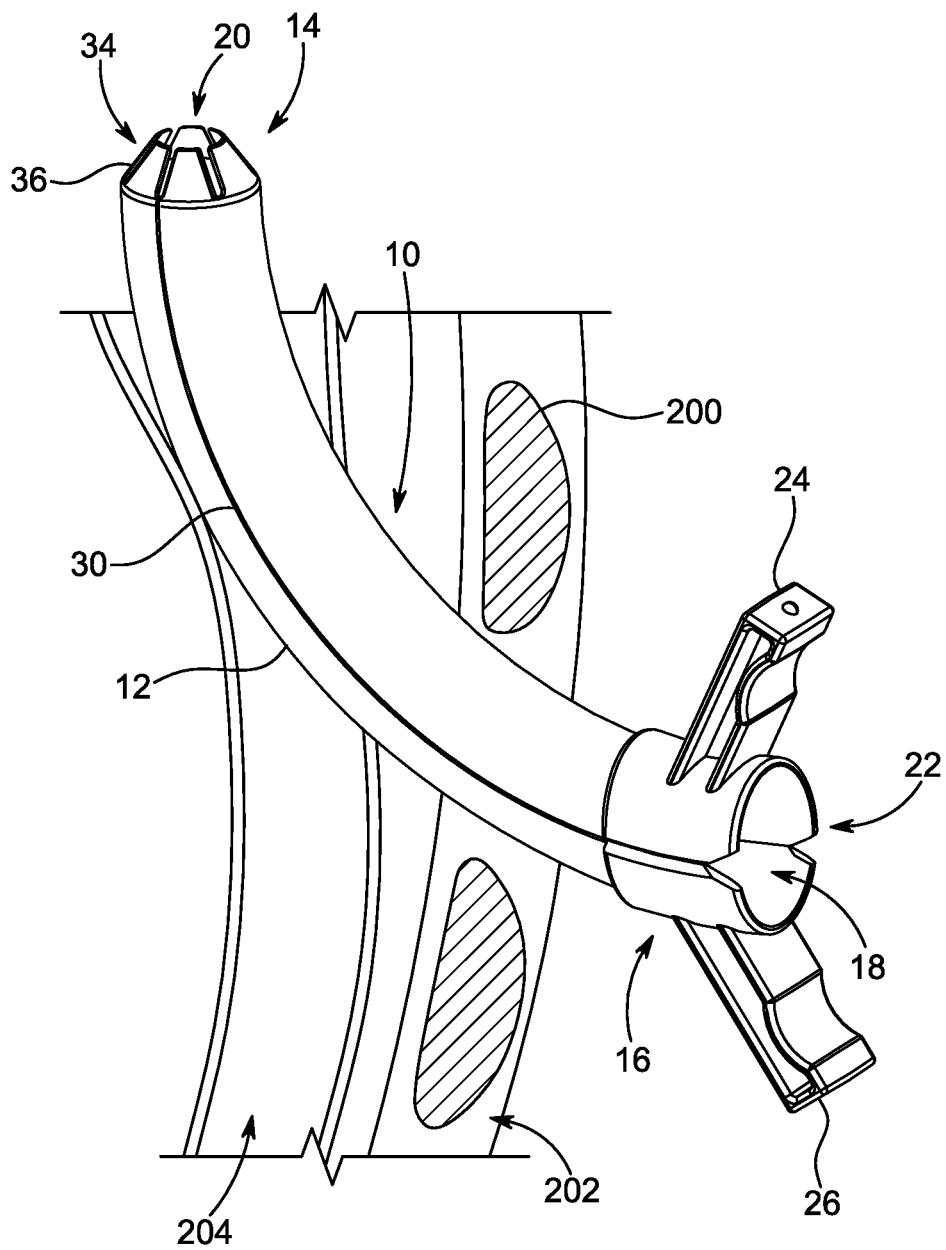
FIG. 15 is a perspective view of an embodiment of a chest tube insertion device with an empty lumen.
Figure 16A:
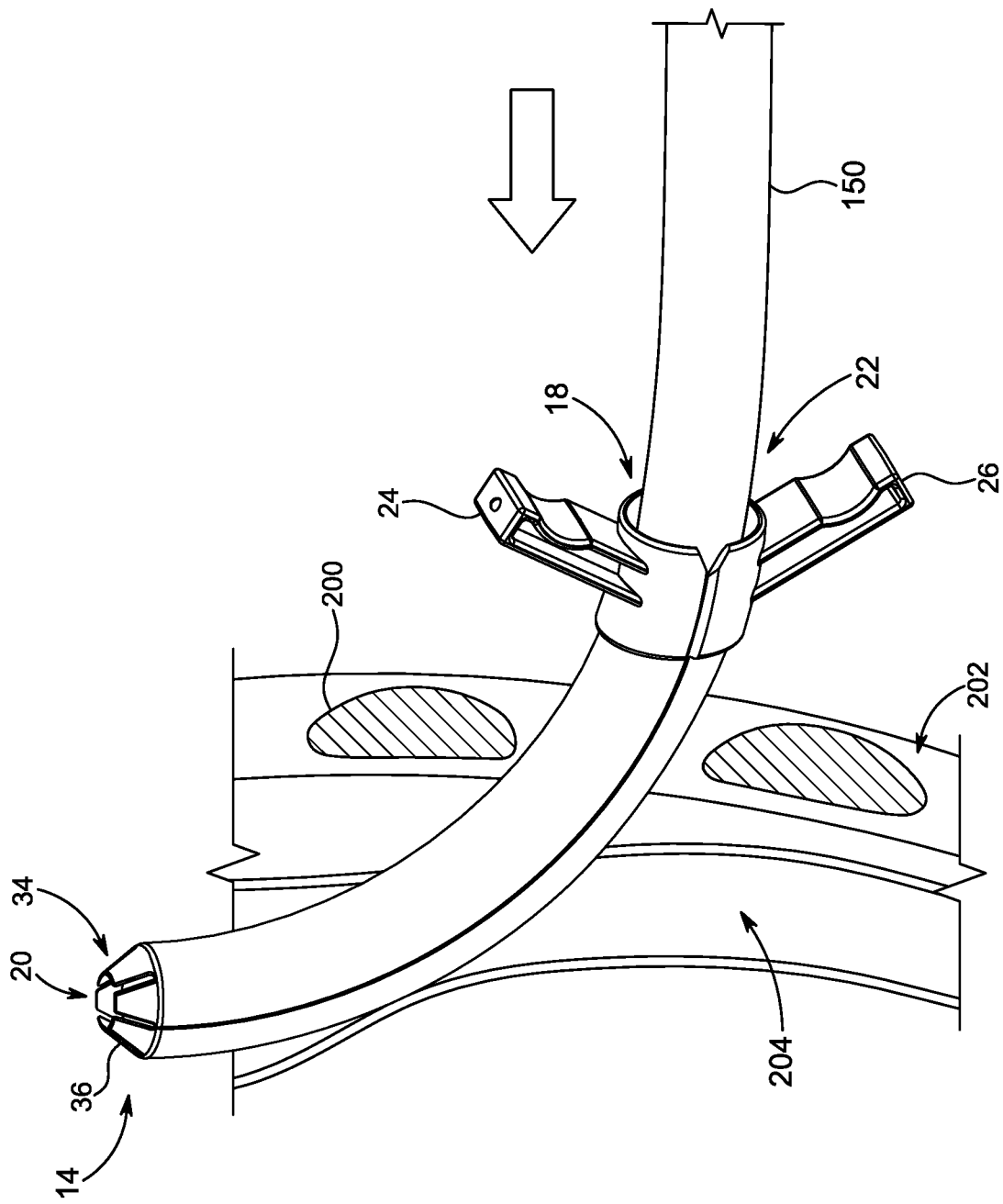
FIGS. 16a and 16b are perspective views of an embodiment of a chest tube insertion device into which a chest tube is being installed.
Figure 16B:
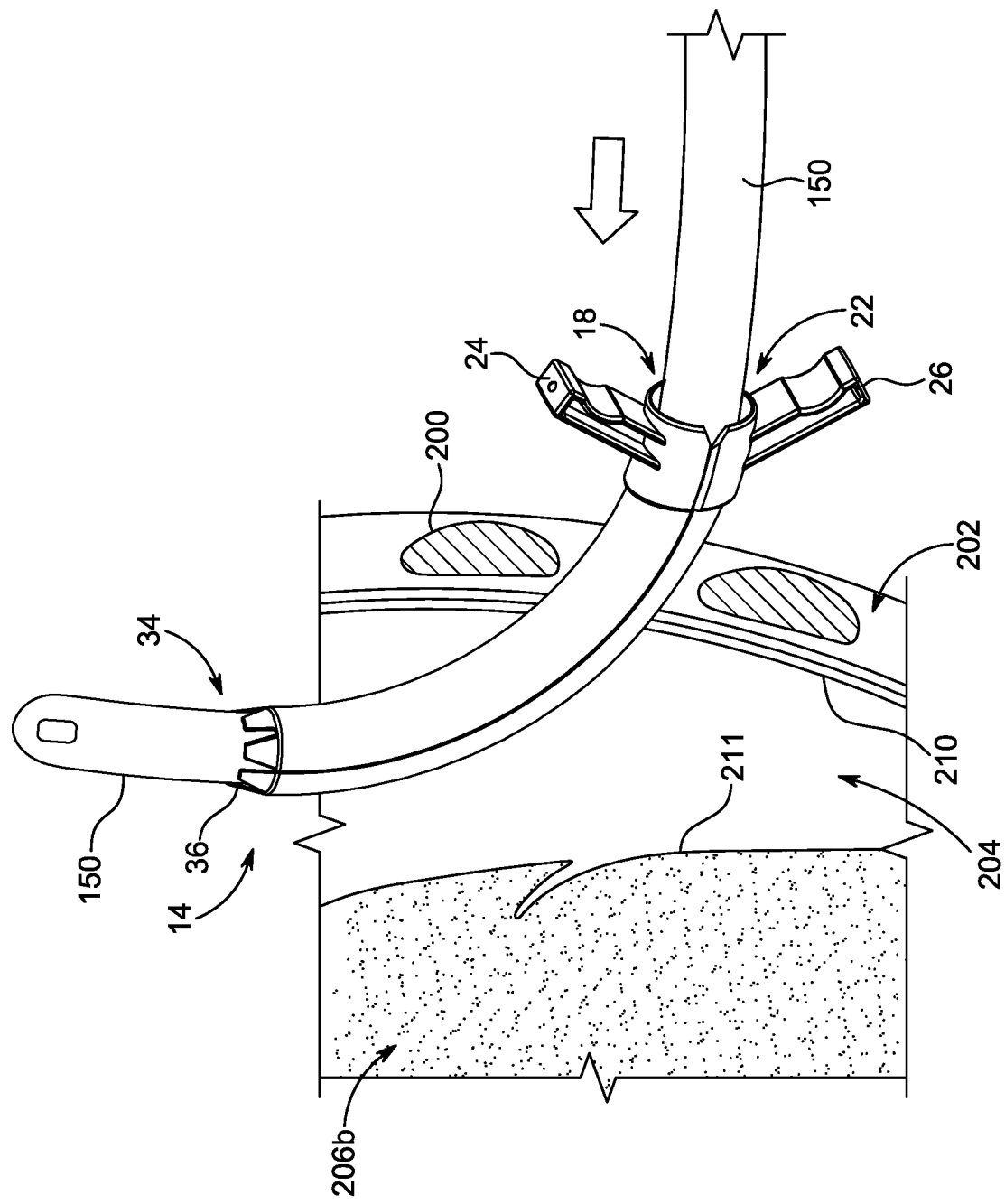

With reference to FIGS. 15, 16a, and 16b, the insertion device 10 may be positioned between the ribs 200 with the distal opening 20 positioned in the pleural space 204 and the proximal opening 22 positioned exterior to the patient. A chest tube 150 may be inserted through the proximal opening 22 of the insertion device 10, fed through the lumen 18, and passed through the distal opening 20 into the pleural space 204. In some embodiments, the tube clamp 34 may engage the chest tube 150 such that the chest tube 150 is retained in the distal opening 20 of the insertion device 10 until a threshold force is applied to overcome the resistance provided to the chest tube 150 by the tube clamp 34. For example, the clamp tabs 36 may contact the chest tube 150 and prevent the chest tube 150 from translating axially within the distal opening 20 when the insertion sheath 10 is being repositioned within the pleural space 204. In some embodiments, the insertion device 10 may be partially opaque to an X-ray such that the position of the insertion device 10 within the pleural space 204 may be visible when an X-ray is taken. This allows the user to appropriately position the chest tube 150 within the pleural cavity 204 before and after the chest tube 150 has been installed in the insertion device 10.

Figure 17:
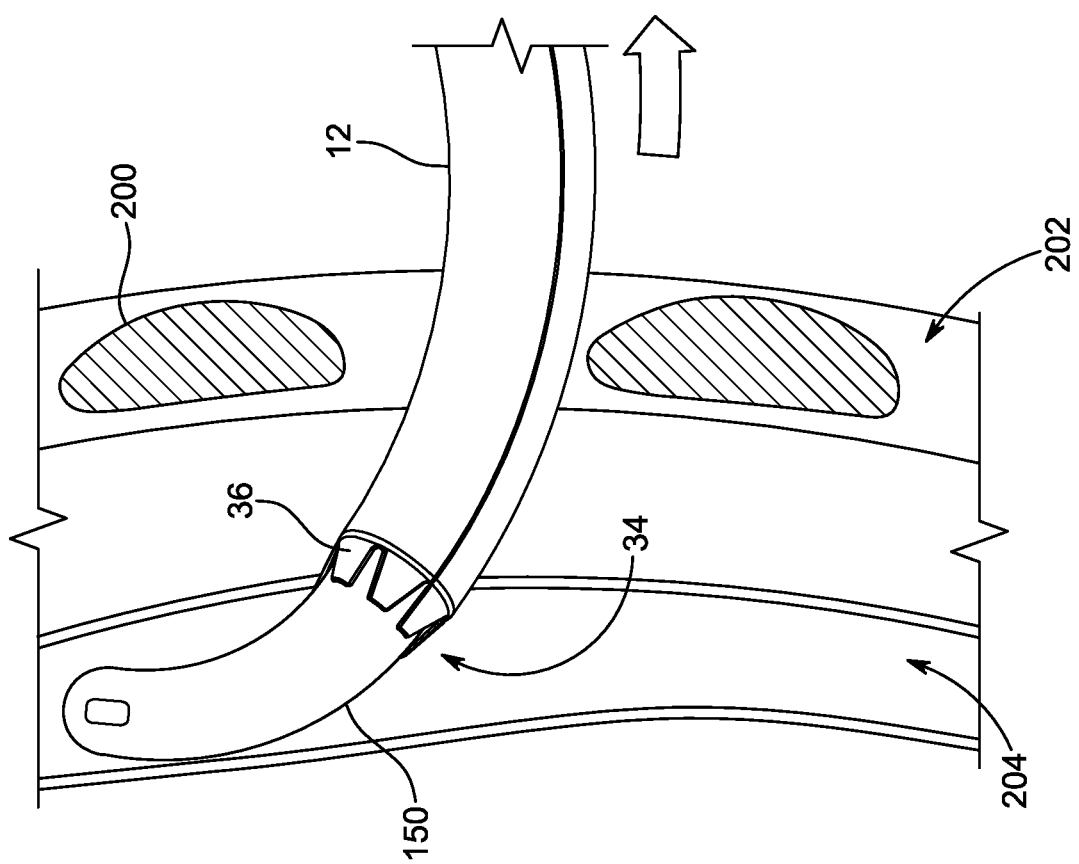
FIG. 17 is a perspective view of an embodiment of a chest tube insertion device being removed from the pleural space of a patient after a chest tube is installed in the pleural space.

Referring now to FIG. 17, once the chest tube 150 has been placed at the desired position within the pleural space 204, the insertion device 10 may be removed from the patient's chest cavity. This can be accomplished by retaining the chest tube 150 in its position while translating the insertion device 10 along the chest tube 10 until the distal end 14 has been removed from the pleural space 204, the intercostal space 202, and out of the patient's body. Accordingly, the chest tube 150 remains in the position into which it was inserted and the insertion device 10 is clear from the patient's body.

Figure 18:
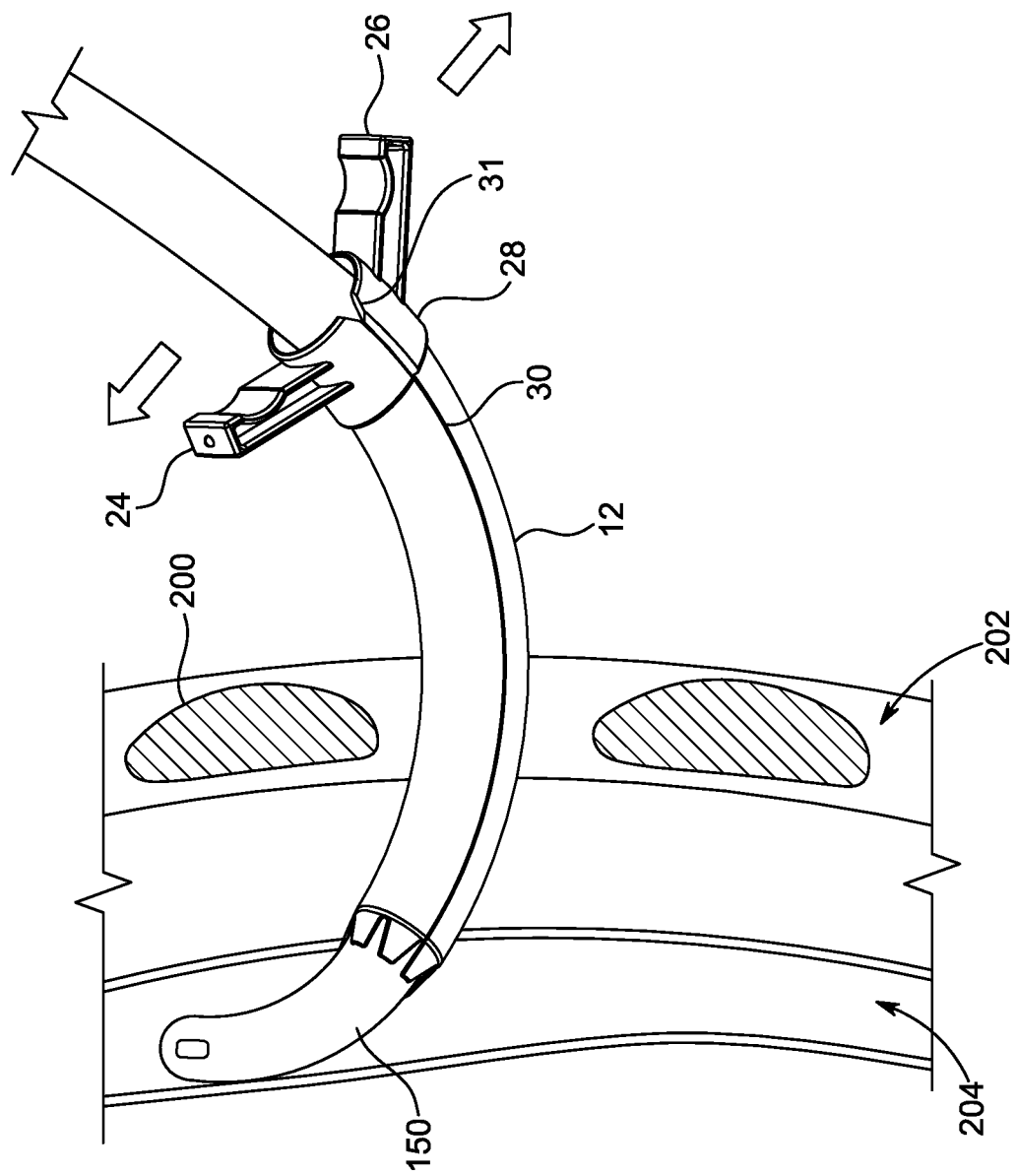
FIG. 18 is a perspective view of an embodiment of a chest tube insertion device being removed from the pleural space of a patient and the handles of the insertion device being pulled in opposite directions to remove the insertion device from off of the chest tube.
Figure 19:
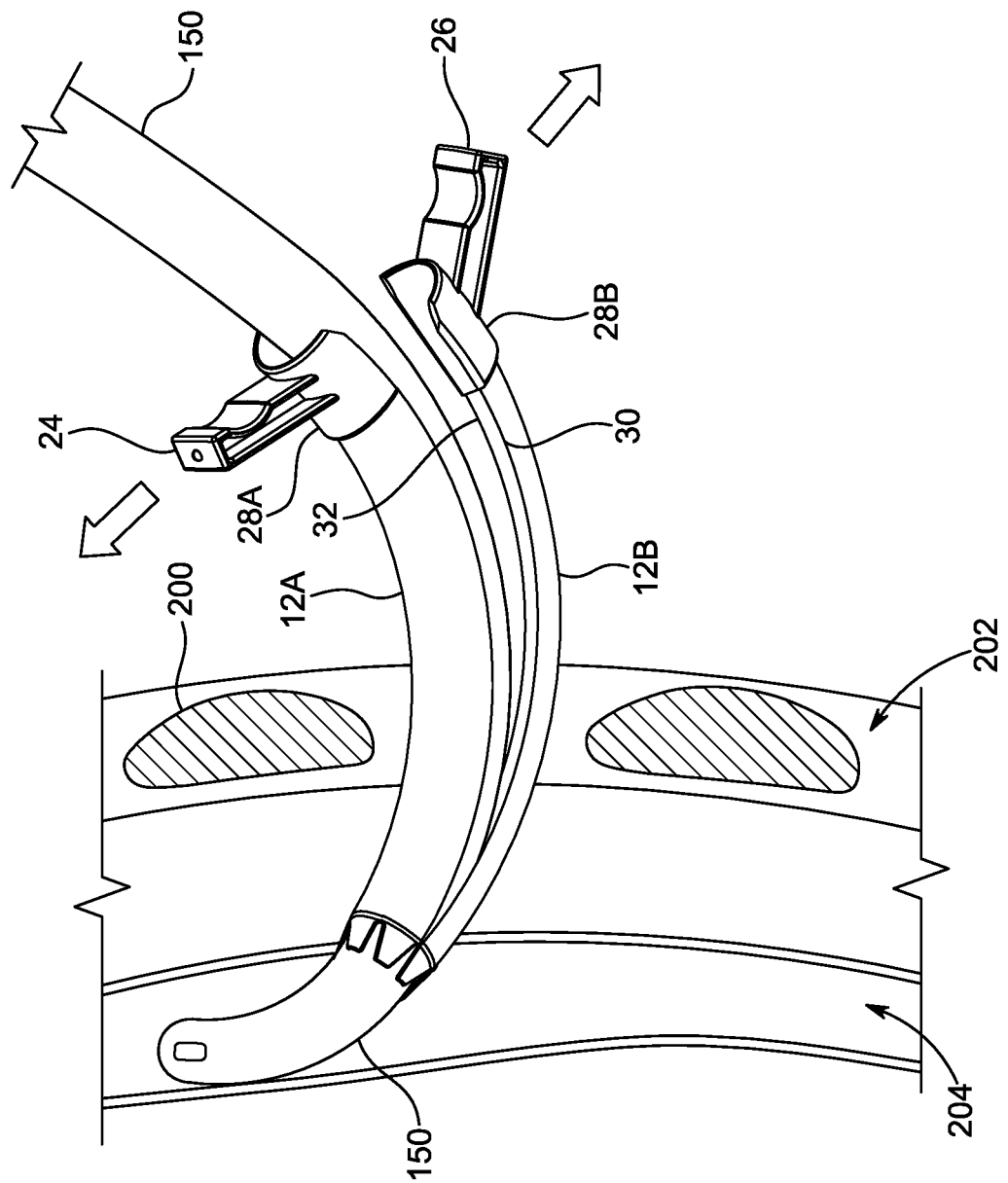
FIG. 19 is perspective view of an embodiment of a chest tube insertion device being removed from a chest tube by forming tears along grooves disposed on the insertion device.

Referring to FIGS. 18-19, once at least a portion of the sheath body 12 is clear from the intercostal space 202, the insertion device 10 is still disposed about the chest tube 150 and may require removal. In some embodiments, the opposite end of the chest tube 150 may be free and the insertion device 10 may be slid off from the opposite end. However, in some embodiments, the chest tube 150 may not have a free end and cannot be removed in this manner. Thus, the present disclosure includes an embodiment in which the insertion device 10 may be separated. For example, the user may separate the insertion device 10 by grasping the handles 24, 26 and pulling the handles 24, 26 in opposite directions. For example, the handles 24, 26 may be pulled apart in a direction perpendicular to the axis 15 at the proximal end 16. A tear begins to form at the proximal end 16 of the insertion device 10 when the handles 24, 26 are pulled apart. This may be facilitated by the notches 31, 33 at the proximal end 16, in some embodiments. The tear may expand as the first side and second side of the sheath body 12a, 12b are further separated. The tear may run along the first and second grooves 30, 32. Thus, the first and second grooves 30, 32 provide and form a fracture line along the length of the insertion device 10.

Figure 20:
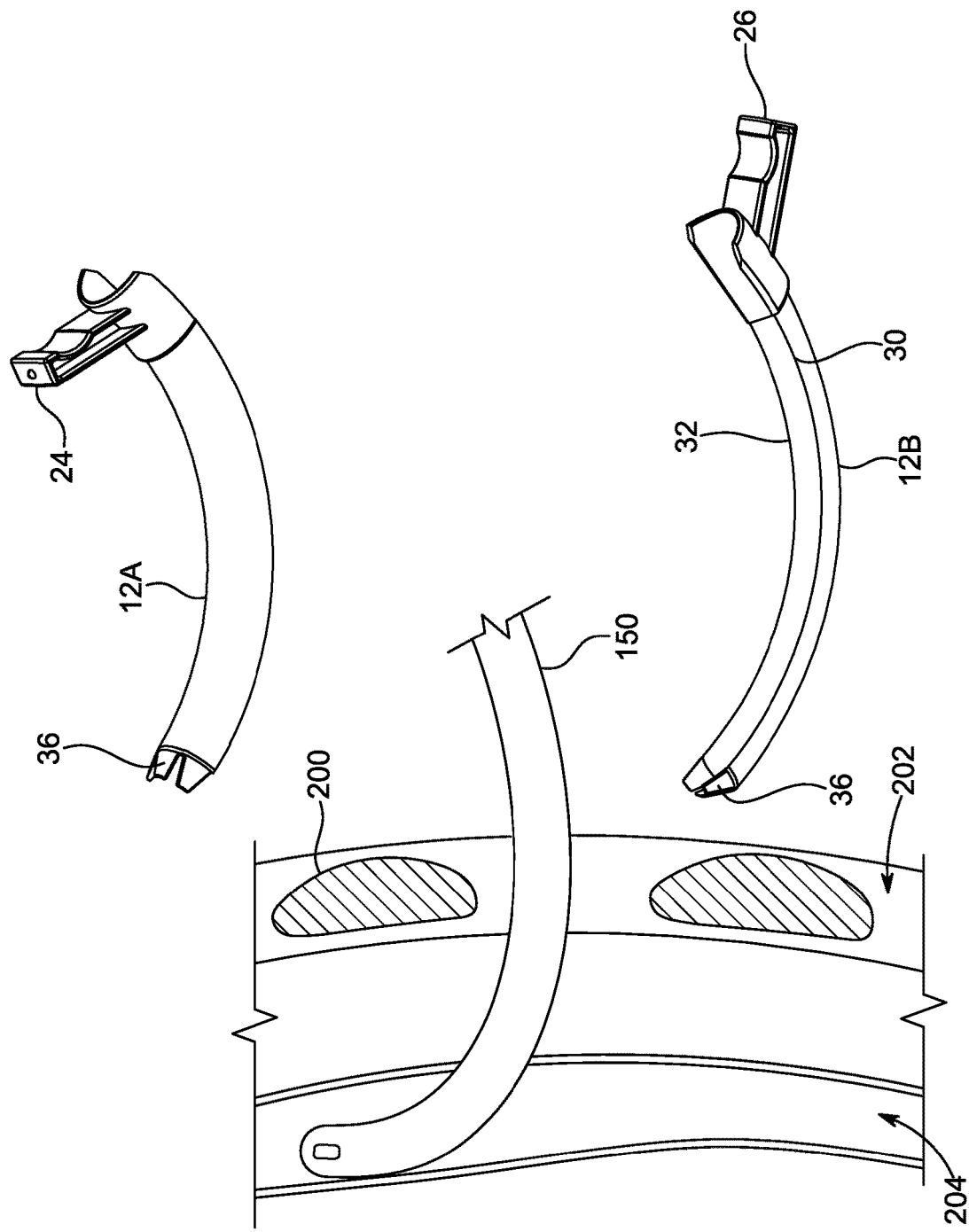
FIG. 20 is a perspective view of an embodiment of a chest tube insertion device that has been removed from off of a chest tube.

Now referring to FIG. 20, the insertion device 10 may be fully removed from the chest tube 150. Once the insertion device 10 is removed from the chest tube 150, the user may secure the chest tube 150 to the patient using traditional procedures. In those embodiments in which the insertion device 10 is removed from the chest tube 150 by separating the insertion device 10 into two portions, the insertion device 10 may be disposable or a one-time-use device. The two halves may be appropriately disposed of in order to maintain a sanitary environment for patients.

Figure 21:
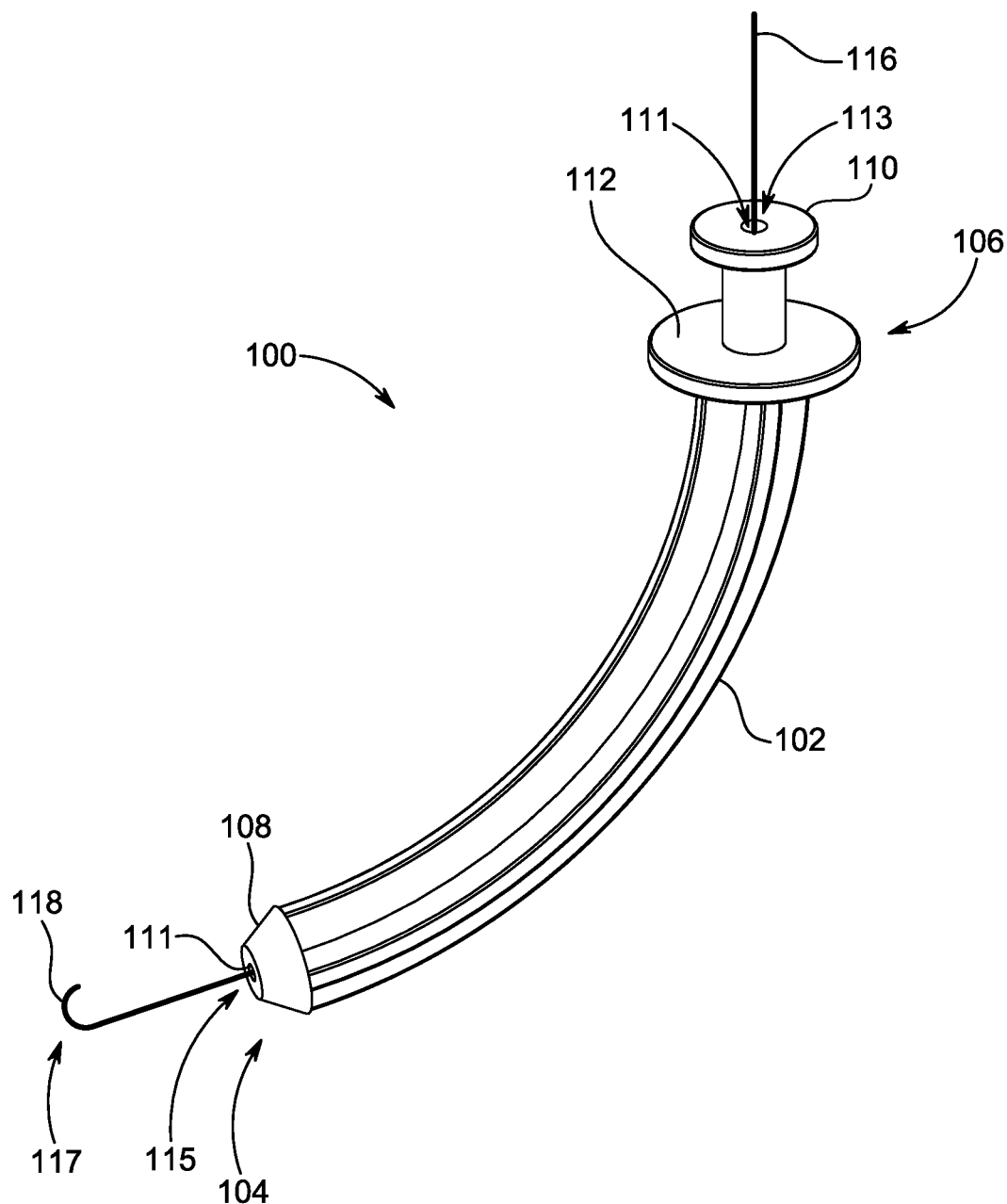
FIG. 21 is a perspective view of an embodiment of a stylet having an interior passage through which a guide wire may pass.
Figure 22:
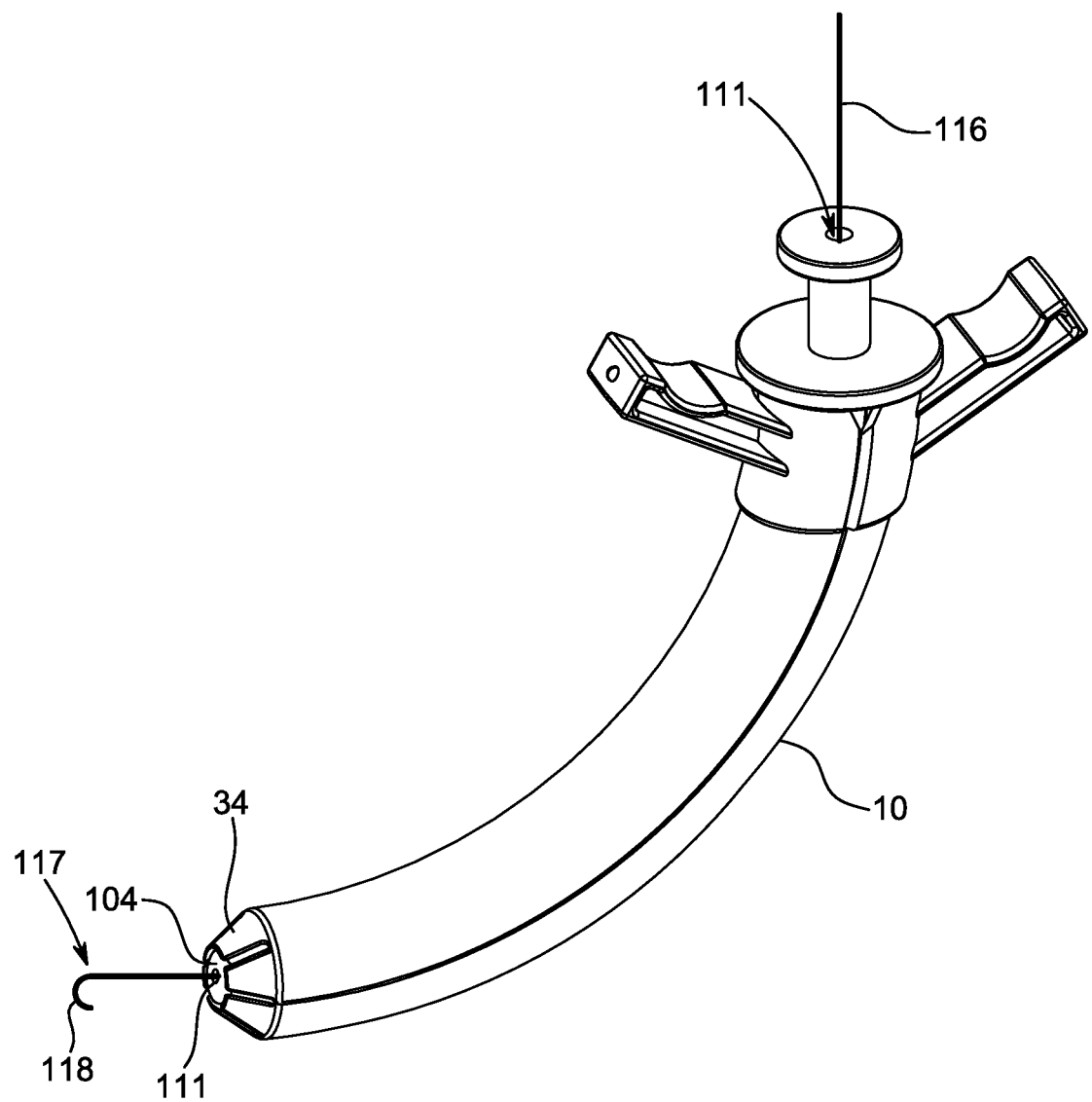
FIG. 22 is a perspective vie of an embodiment of an insertion device with a stylet installed therein, the stylet having an interior passage through which a guidewire may pass.

In some embodiments, the insertion device 10 may be advanced into the intercostal space 204 along a guidewire 116. FIGS. 21 and 22 demonstrate an alternative embodiment in which the insertion device 10 may be advanced along a guidewire 116. As seen in FIG. 21, specifically, the stylet 100 may include an interior stylet lumen 111, which runs from a proximal end 106 to a distal end 104 of the stylet 100 and has a proximal opening 113 and a distal opening 115. The stylet lumen 111 may be disposed about the axis 15.

FIG. 22 demonstrates one embodiment in which the stylet 100 is installed into the insertion device 10, and the stylet lumen 111 and the stylet 100 are aligned around the same axis 15 about which the insertion device 10 and the lumen 18 are oriented. This embodiment, in which the stylet 100 includes a stylet lumen 111, may be used with various surgical techniques, including the Sedlinger technique. For example, a surgeon may insert a trochar through the intercostal space 202 into the pleural cavity 204. With a trochar inserted, the surgeon may insert the guidewire 116 through the trochar and such that the distal end 117 of the guidewire 116 is positioned in the pleural cavity 204. The guidewire 116 may be positioned in the appropriate space with the aid of ultrasound technology.

Once the guidewire 116 is positioned where the surgeon desires, the trochar may be removed from the patient. The stylet 100 installed into the insertion device 10 may than be used in conjunction with the guidewire 116. This may be accomplished by installing the free end of the guidewire 116 into the distal opening 115 of the stylet 100. The stylet 100 and insertion device 10 may be advanced along the guidewire 116 until the insertion device 110 is appropriately positioned in the pleural cavity 204. Once the positioning is correct, the guidewire 116 may be removed from the patient by translating the guidewire 116 through stylet lumen 111. The surgeon may continue to position the insertion device 10 after the guidewire has been removed. Once the insertion device 10 is correctly positioned, the stylet 100 may be removed from the insertion device 10. This is an alternative method for the insertion of insertion device 10 and may continue with the remainder of the method disclosed herein of insertion of the chest tube 150 and the removal of the insertion device 10.

This technique of using a guidewire 116 during the installation of the insertion device 10 with the stylet 100 positioned therein may draw from the Seldinger Technique. In some embodiments, as seen in FIGS. 21 and 22, the guidewire 116 may include a curved tip 118 at a distal end 117 of the guidewire 116.

Thus, although there have been described particular embodiments of the present invention of a new and useful CHEST TUBE INSERTION SHEATH, it is not intended that such references be construed as limitations upon the scope of this invention.

What is claimed is:

1. A chest tube insertion sheath apparatus for positioning a chest tube in a pleural space in a chest cavity of a patient, comprising: a chest tube insertion sheath including a sheath body disposed about a curvilinear axis and having a distal end and a proximal end, wherein the sheath body comprises a rigid material; and a lumen defined axially through the chest tube insertion sheath from the distal end to the proximal end along the curvilinear axis, the lumen including a distal end opening at the distal end and a proximal end opening at the proximal end, wherein the lumen is open from the distal end opening to the proximal end opening, and a tapered tube clamp at the distal end of the sheath body, the tube clamp including a plurality of clamp tabs in spaced relation to each other, separated by a clamp tab gap and angled radially inward toward the distal end opening, wherein the distal end opening has a first diameter when the plurality of clamp tabs are in a non-flexed position and a second diameter when the plurality of clamp tabs are in a flexed position and wherein the second diameter is larger than the first diameter.

2. The apparatus of claim 1, wherein the chest tube insertion sheath is configured to orient the distal end of the sheath body in superior, inferior, anterior, posterior, medial and lateral directions in the pleural space by rotating the sheath body such that the curvilinear axis moves relative to the pleural space.

3. The apparatus of claim 1, wherein the sheath body is configured be removed from the chest tube by splitting the sheath body into two portions while the chest tube remains inserted in the patient a desired location in the pleural space.

4. The apparatus of claim 1, further comprising a chest tube disposed in the chest tube insertion sheath.

5. The apparatus of claim 4, wherein the chest tube comprises a distal tube end extending from the proximal end opening of the lumen into the pleural space when the chest tube insertion sheath and chest tube are both positioned in the chest cavity of the patient.

6. The apparatus of claim 1, further comprising:
a first groove on the sheath body extending from the distal end to the proximal end of the sheath body, the first groove forming a first fracture line; and
a second groove on the sheath body extending from the distal end to the proximal end of the sheath body, the second groove forming a second fracture line,
wherein the sheath body is configured to tear into separate pieces along the first and second fracture lines.

7. The apparatus of claim 6, further comprising a first handle and a second handle positioned on the proximal end of the sheath body, the first handle positioned between the first groove and the second groove on a first side of the sheath body and the second handle positioned opposite the first handle between the first groove and the second groove on a second side of the sheath body.

8. The apparatus of claim 7, wherein the sheath body is configured to be positioned toward the desired location in the pleural space by rotating the chest tube insertion sheath via the first and second handles.

9. The apparatus of claim 8, further comprising:
a first notch positioned on the proximal end of the sheath body and positioned at the first groove; and
a second notch positioned on the proximal end of the sheath body and positioned at the second groove.

10. The apparatus of claim 9, further comprising a rigid stylet disposed in the chest tube insertion sheath.

11. The apparatus of claim 10, further comprising a guidewire disposed in the stylet.

12. A chest tube insertion sheath apparatus for inserting a chest tube into a pleural space in a chest cavity of a patient, comprising: a chest tube insertion sheath oriented about a curvilinear axis, the chest tube insertion sheath including a rigid sheath body and having a distal end and a proximal end; a lumen defined axially along the curvilinear axis through the chest tube insertion sheath from the distal end to the proximal end, the lumen including a distal end opening at the distal end and a proximal end opening at the proximal end, wherein the lumen is open from the distal end opening to the proximal end opening; and a chest tube positioned through the chest tube insertion sheath between the proximal end opening and the distal end opening, wherein the chest tube comprises a distal tube end extending from the distal end of the chest tube insertion sheath, first and second handles disposed on the proximal end of the chest tube insertion sheath and a tapered tube clamp at the distal end of the sheath body, the tube clamp including a plurality of clamp tabs in spaced relation to each other, separated by a clamp tab gap and angled radially inward toward the distal end opening, wherein the distal end opening has a first diameter when the plurality of clamp tabs are in a non-flexed position and a second diameter when the plurality of clamp tabs are in a flexed position and wherein the second diameter is larger than the first diameter.

13. The apparatus of claim 12, wherein the chest tube insertion sheath is configured to position the distal end of the sheath body in superior, inferior, anterior, posterior, medial and lateral directions in the pleural space by rotating the sheath body via the first and second handles.

14. The apparatus of claim 12, wherein the chest tube insertion sheath is configured be removed from the chest tube by splitting the chest tube insertion sheath into two portions while the chest tube remains inserted in the patient a desired location in the pleural space in the chest cavity of the patient.

15. The apparatus of claim 12, wherein the chest tube is moveable axially along the chest tube in a direction away from the patient while the chest tube remains inserted in the patient at the desired location in the pleural space in the chest cavity of the patient.

16. The apparatus of claim 15, further comprising first and second fracture lines defined on the sheath body.

17. A method of inserting a chest tube into pleural space in a chest cavity of a patient, comprising: providing a chest tube having a distal tube end; making an incision in a chest of the patient; inserting a chest tube insertion sheath through the incision and through an intercostal space between ribs of the patient into the pleural space in the chest cavity of the patient, the chest tube insertion sheath comprising a rigid sheath body oriented along a curvilinear axis and having a curvilinear shape, the chest tube insertion sheath having a distal end, a proximal end and a lumen defined axially through the sheath body from the distal end to the proximal end of the sheath body along the curvilinear axis; and a tapered tube clamp at the distal end of the sheath body, the tube clamp including a plurality of clamp tabs in spaced relation to each other, separated by a clamp tab gap and angled radially inward toward the distal end opening, wherein the distal end opening has a first diameter when the plurality of clamp tabs are in a non-flexed position and a second diameter when the plurality of clamp tabs are in a flexed position and wherein the second diameter is larger than the first diameter; positioning the distal end of the chest tube insertion sheath in the pleural space in the chest cavity by rotating the rigid and curved sheath body relative to the patient such that the curvilinear shape of the sheath body forces the distal end of the sheath body to a desired location in the pleural space in the chest cavity; inserting the chest tube through the chest tube insertion sheath via the lumen in the sheath body such that the distal tube end of the chest tube extends from the distal end of the sheath body into the pleural space in the chest cavity at the desired location; and removing the chest tube insertion sheath from the chest of the patient by splitting the sheath body into separate pieces while the distal tube end of the chest tube remains at the desired location in the pleural space in the chest cavity of the patient.

18. The method of claim 17, further comprising retaining the chest tube at the desired location in the pleural space in the chest cavity while translating the chest tube insertion sheath axially along the chest tube away from the chest cavity of the patient until the distal end of the sheath body is outside the pleural space in the chest cavity prior to splitting the sheath body into separate pieces.

19. The method of claim 17, further comprising retaining the chest tube at the desired location in the pleural space in the chest cavity while translating the chest tube insertion sheath axially along the chest tube away from the chest cavity of the patient until the distal end of the sheath body is outside the patient's body prior to splitting the sheath body into separate pieces.

20. The method of claim 17, wherein the chest tube insertion sheath comprises first and second handles.

21. The method of claim 20, further comprising orienting the distal end of the sheath body toward the desired location in the pleural space in the chest cavity by rotating the sheath body via the first and second handles.

22. The method of claim 20, further comprising orienting the distal end of the sheath body toward the desired location in pleural space in the chest cavity by rotating the proximal end of the sheath body via the first and second handles without pivoting the articulating the proximal end of the sheath body in the intercostal space.

23. The method of claim 22, further comprising taking an X-ray of the chest cavity while the chest tube insertion sheath is in the pleural space.

* * * * *